United States Patent
Petit et al.

(10) Patent No.: US 10,391,172 B2
(45) Date of Patent: Aug. 27, 2019

(54) USE OF NANODIAMONDS FOR GENERATING FREE RADICALS FOR THERAPEUTIC PURPOSES UNDER RADIATION

(71) Applicant: Commissariat A L'Energie Atomique Et Aux Energies Alternatives, Paris (FR)

(72) Inventors: Tristan Petit, Paris (FR); Jean-Charles Arnault, Rambouillet (FR); Hugues Girard, Viroflay (FR); Romain Grall, Fontenay aux Roses (FR); Sylvie Chevillard, Paris (FR); Jozo Delic, Bourg la Reine (FR)

(73) Assignee: Commissariat a L'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 14/413,594

(22) PCT Filed: Jul. 12, 2013

(86) PCT No.: PCT/IB2013/055766
§ 371 (c)(1),
(2) Date: Jan. 8, 2015

(87) PCT Pub. No.: WO2014/009930
PCT Pub. Date: Jan. 16, 2014

(65) Prior Publication Data
US 2015/0182624 A1   Jul. 2, 2015

(30) Foreign Application Priority Data

Jul. 13, 2012   (FR) ..................................... 12 56781
Jul. 13, 2012   (FR) ..................................... 12 56786
Nov. 16, 2012   (FR) ..................................... 12 60924

(51) Int. Cl.
*C01B 32/25*   (2017.01)
*A61K 41/00*   (2006.01)
(Continued)

(52) U.S. Cl.
CPC ........ *A61K 41/0038* (2013.01); *A61K 9/0009* (2013.01); *A61K 9/5115* (2013.01);
(Continued)

(58) Field of Classification Search
CPC ........ G01N 21/66; B82Y 10/00; B82Y 30/00; Y10T 428/2982; Y10T 428/2991;
(Continued)

(56) References Cited

U.S. PATENT DOCUMENTS

2007/0181121 A1* 8/2007 Whalen ................ A61G 10/023
128/202.12
2008/0003183 A1   1/2008 Ting
(Continued)

OTHER PUBLICATIONS

Khabashesku et al., Functionalized carbon nanotubes and nanodiamonds for engineering and biomedical applications, Diamond & Related Materials, 14 (2005) 859-866).*
(Continued)

Primary Examiner — Hoa (Holly) Le
(74) Attorney, Agent, or Firm — Alston & Bird LLP

(57) ABSTRACT

The present invention relates to the use of nanodiamonds as drugs generating free radicals, in particular for treating tumors. The invention is based on generating free radicals on the surface of the nanodiamonds when they are exposed to radiation, for example ionizing radiation. In order to increase the effectiveness of the nanodiamonds, the nanodiamonds can be complexed with a radiosensitizing agent, such as a chemical molecule or an interfering RNA targeting a repairing gene.

20 Claims, 19 Drawing Sheets

(51) Int. Cl.
| | |
|---|---|
| A61K 9/00 | (2006.01) |
| A61K 9/51 | (2006.01) |
| B82Y 5/00 | (2011.01) |
| A61K 31/713 | (2006.01) |
| A61N 5/06 | (2006.01) |
| A61N 5/10 | (2006.01) |
| C12N 15/113 | (2010.01) |
| A61K 47/69 | (2017.01) |

(52) U.S. Cl.
CPC ........ *A61K 31/713* (2013.01); *A61K 47/6921* (2017.08); *A61N 5/062* (2013.01); *A61N 5/10* (2013.01); *B82Y 5/00* (2013.01); *C01B 32/25* (2017.08); *C12N 15/1137* (2013.01); *A61N 2005/0661* (2013.01); *A61N 2005/1087* (2013.01); *A61N 2005/1091* (2013.01); *C12N 2310/14* (2013.01); *C12N 2310/351* (2013.01); *C12N 2320/30* (2013.01); *Y10T 428/2982* (2015.01)

(58) Field of Classification Search
CPC ...... A61K 41/0038; A61K 5/10; C01B 32/25; A61N 5/10; A61N 5/1019; A61N 5/1098; A61N 2005/0661; A61N 2005/1087
USPC .......................................................... 428/403
See application file for complete search history.

(56) References Cited

U.S. PATENT DOCUMENTS

| | | | | |
|---|---|---|---|---|
| 2009/0069611 | A1* | 3/2009 | Lukehart | B82Y 30/00 585/250 |
| 2010/0069567 | A1* | 3/2010 | Petrov | B82Y 30/00 524/560 |
| 2010/0305309 | A1 | 12/2010 | Ho et al. | |
| 2011/0006218 | A1* | 1/2011 | Mochalin | B82Y 30/00 250/459.1 |
| 2011/0008447 | A1 | 1/2011 | Chao et al. | |
| 2011/0045480 | A1* | 2/2011 | Fournier | C12Q 1/6886 435/6.16 |
| 2011/0286943 | A1* | 11/2011 | Sung | B82Y 30/00 424/59 |

OTHER PUBLICATIONS

Med Device Online, Nanodiamond Drug Device Could Transform Cancer Treatment, Oct. 6, 2008.*
Wang et al., Development of NGR peptide-based agents for tumor imaging, Am. J. Nucl. Med. Mol. Imaging; 1(1):36-46 (2011).*
Alonso, Hadron Particle Therapy, 1996 IEEE, 58-62, 1996.*
Arnault et al., Surface chemical modifications and surface reactivity of nanodiamonds hydrogenated by CVD plasma, Phys. Chem. Chem. Phys., 2011, 13, 11481-11487).*
Barnhart et al., Structural transformations in carbon nanoparticles induced by electron irradiation, 2002.*
Santacruz-Gomez et al, Carboxylated nanodiamonds inhibit γ-irradiation damage of human red blood cells, Nanoscale, 2016, 8, 7189.*
Korolkov et al., Dual reaction capacity of hydrogenated nanodiamond, Diamond & Related Materials, 16 (2007) 2129-2132.*
Williams et al., Size-dependent reactivity of diamond nanoparticles, ACS Nano, vol. 4, No. 8, 4824-4830 (2010) (Year: 2010).*
Petit et al., Early stages of surface graphitization on nanodiamond probed by X-ray photoelectron spectroscopy, Physical Review B 84, 233407 (2011) (Year: 2011).*
Petit, Modications de surface des nanodiamants : comprehension des mecanismes d'echanges electroniques et mise en evidence d'un effet theerapeutique, Thesis, Apr. 2013 (Year: 2013).*
Water et al, Water Radiolysis: Influence of Oxide Surfaces on H2 Production under Ionizing Radiation, Water 2011, 3, 235-253; doi:10.3390/w3010235 (Year: 2011).*
Chakrapani et al., Charge Transfer Equilibria Between Diamond and an Aqueous Oxygen Electrochemical Redox Couple, Science 318 (5855), 1424-1430, Nov. 2007. (Year: 2007).*
International Search Report and Written Opinion for Application No. PCT/IB2013/055766 dated Nov. 6, 2013.
Arnault, J-C, et al., *Surface Chemical Modifications and Surface Reactivity of Nanodiamonds Hydrogenated by CVD Plasma*, Phys. Chem. Chem. Phys., vol. 13, No. 24 (Jun. 2011) 11481-11487 (XP-002697337).
Fu, C-C., et al., *Characterization and Application of Single Fluorescent Nanodiamonds as Cellular Biomarkers*, PNAS, vol. 104, No. 3 (Jan. 2007) 727-732 (XP-002456036).
Girard, H. A. et al., *Surface Properties of Hydrogenated Nanodiamonds: A Chemical Investigation*, Phys. Chem. Chem. Phys., vol. 13, No. 24 (Jun. 2011) 11517-11523 (XP-002697336).
Kuznetsov, O. et al., *Water-Soluble Nanodiamond*, Langmuir, vol. 28m, No. 11 (Mar. 2012) 5243-5248 (XP-002697335).
Batsanov, S. S. eta l., *Giant Dielectric Permittivity of Detonation-Produced Nanodiamond is Caused by Water*, Journal of Materials Chemistry, 22 (2012) 11166-11172.
Begg, A. C. et al., *Strategies to Improve Radiotherapy With Targeted Drugs*, Nature Review Cancer, 11 (2011) 239-253.
Chakrapani, J. C. et al., *Charge Transfer Equilibria Between Diamond and an Aqueous Oxygen Electrochemical Redox Couple*, Science, 318 (2007) 1424:30.
Chang, Y.-R. et 31., *Mass Production and Dynamic Imaging of Fluorescent Nanodiamonds*, Nature Nanotechnology, 3 (2008) 284-288.
Chao, J. I. et al., *Nanometer-sized Diamond Particle as a Probe for Biolabeling*, Biophysical Journam, 93 (2007) 2199-2208(2).
Chen, M. et al., *Nanodiamond Vectors Functionalized with Polyethylenimine for siRNA Delivery*, The Journal of Physical Chemistry Letters, 1 (2010) 3167-3171.
Chen, X. et al., *2', 7'-Dichlorodihydrofluorescein as a Fluorescent Probe for Reactive Oxygen Species Measurement: Forty Years of Application and Controversy*, Free Radical Research, 44(6) (2010) 587-604.
Curnis, F. et al., *Differential Binding of Drugs Containing the NGR Motif to CD13 Isoforms in Tumor Vessels, Epithelia, and Myeloid Cells*, Cancer Research, 62(3)(2002) 867-74.
Girard, H. A. et al., *Hydrogenation of Nanodiamonds Using MPCVD: A New Route Toward Organic Functionalization*, Diamond and Related Materials, 19 (2010) 1117-1123.
Higgins, G. S. et al., *A Small Interfering RNA Screen of Genes Involves in DNA Repair Identifies Tumor-Specific Radiosensitization by POLQ Knockdown*, Cancer Research, 70(2010) 2984-2993.
Huang, LC et al., *Adsorption and Immobilization of Cytochrome C on Nanodiamonds*, Langmuir, 20(14) (2004) 587-984.
Jarre, G. et al., *Playing the Surface Game-Diels-Alder Reactions on Diamond Nanoparticles*, Chemical Communication (Cambridge) 47 (2011) 544-546.
Kruger, A. et al., *Surface Functionalisation of Detonation Nanodiamond Suitable for Biological Applications*, Journal of Material Chemistry, 11 (2006) 2322-2328.
Petit, T. et al., *Early Stages of Surface Graphitization on Nanodiamond Probed by X-ray Photoelectron Spectroscopy*, Physical Review B, 84 (2011), 233-407.
Ryu, L. eet al., *Atmospheric Oxygen Binding and Hole Doping in Deformed Grapheme on a SiO2 Substrate*, Nano Letters, 10 (2010) 4944-4951.
Yang, K. et al., *Graphene in Mice: ultrahigh In Vivo Tumor Uptake and Efficient Photothermal Therapy*, Nano Letters 10 (2010) 3318-3323.
Kuznetsov et al., "Water-soluble nanodiamonds.", Langmuir : The ACS Journal of Surfaces and Colloids Mar. 20, 2012, (Mar. 20, 2012), vol. 28, No. 11, ISSN 1520-5827, pp. 5243-5248.
Office Action for European Application No. 13766397.7 dated Dec. 20, 2016, 6 pages.

* cited by examiner

USE OF NANODIAMONDS FOR GENERATING FREE RADICALS FOR THERAPEUTIC PURPOSES UNDER RADIATION

FIELD

The present invention relates to the radiotherapy field. The subject thereof is in particular the use of particular diamond nanoparticles (or nanodiamonds) for locally generating free radicals.

BACKGROUND

Radiotherapy is a common technique for treating cancerous tumors, used in approximately 50% of cases. It consists in creating free radicals in the cells by localized irradiation; these free radicals cause breaks in the DNA of the irradiated cells, resulting in their death. The efficacy of radiotherapy treatments is currently limited by the resistance of certain tumors to ionizing radiation, compared with healthy cells. A selective and effective radiosensitization of tumor cells would make it possible to significantly improve the efficacy of these treatments and to reduce the side effects on healthy tissues.

With this aim, various approaches have been described, such as the use of nanoparticles capable of locally generating free radicals, or the use of radiosensitizing agents.

The first approach consists in locally generating free radicals, within the tumor, using nanoparticles. The methods of this type described to date are based on physical properties, associated with the nanoparticles, making it possible to effectively generate free-radical species at their surface under irradiation. The nanoparticles used generally consist of atoms which have a high atomic number (Z), in order to more efficiently absorb X-rays, but they are generally expensive materials (gold, platinum, rare earth elements), and/or can induce toxicity, and/or are not very stable in a biological medium. By way of example, mention may be made of patent application US 2008/0003183 (Ting Guo), which proposes the use of nanoparticles consisting of heavy elements such as gold, capable of locally emitting Auger electrons under irradiation. This generation of electrons can be induced using X-rays having an energy that water molecules absorb only weakly, in order to generate free radicals essentially in the vicinity of the nanoparticles. However, in order to improve the colloidal stability and the biocompatibility of these nanoparticles, the grafting of molecules is often necessary, which can reduce the dose of secondary or Auger electrons transmitted to the environment of the nanoparticle, and therefore reduce the dose of free radicals generated.

According to the second approach mentioned above, new radiosensitizing molecules are currently being studied, the objective of which is to target the biological defenses specific to tumor cells (C. Begg et al, 2011). Unfortunately, these molecules cannot always be delivered into the tumor cells in vivo, thereby limiting their therapeutic use. This is in particular the case with POLQ interfering RNAs, which have recently shown great selectivity in the radiosensitization of tumor cells in vitro (Higgins at al, 2010). It may be difficult to use these interfering RNAs in vivo without a vectorization means, since their bioavailability is limited.

Various biotechnological applications are currently known for nanodiamonds, such as the vectorization and the delivery of medicaments and of interfering RNAs in tumor cells. In these applications, the nanodiamonds are used only as passive vectors. By way of example, mention may be made of patent application US 2010/0305309 (Ho et al.), relating to various processes for delivering medicaments with nanodiamonds. In this particular case, the nanodiamonds used as vectors are surface-oxidized, which gives them a negative surface charge and makes it necessary to add polymers so as to make it possible to vectorize DNA or RNA strands which also have a negative charge. These polymers can induce additional toxicity and significantly increase the size of the nanodiamonds, which can induce a greater retention in organs such as the liver or the kidneys for in vivo applications.

SUMMARY

The present invention is based on the demonstration, by the inventors, of a property of nanodiamonds which has up until now been ignored. The term "nanodiamond" denotes herein any nanoparticle mainly consisting of $sp^3$ hybridized carbon atoms, having a size of less than 250 nm. These nanoparticles can be, inter alia, synthesized by grinding of a synthetic diamond or by detonation. In the latter case, the nanodiamonds generally have a size less than 10 nm. The term "nanodiamond" also denotes aggregates of nanoparticulate size consisting of primary diamond nanoparticles. The inventors have observed that nanodiamonds have particular physical properties which allow them to effectively generate free radicals under radiation, in particular under ionizing radiation. Nanodiamonds in fact consist of a very high concentration of carbon atoms ($1.8 \times 10^{23}$ atoms/cm$^3$), which makes it possible to more efficiently absorb radiation than the surrounding biological tissues, despite an equivalent atomic number. Furthermore, nanodiamonds have very good colloidal stability, even without functionalization that would reduce the transfer of the electrons generated to their environment. Finally, the excellent thermal conductivity of the diamond ensures a very efficient release of the heat resulting from the irradiation (for example by ionizing radiation) at the surface of the nanodiamonds. Nanodiamonds therefore make it possible to effectively generate free radicals in tumor cells, and/or heat, while using a carbon-based material which is inexpensive, biocompatible and stable in a biological medium, without necessary functionalization.

The present invention therefore relates, firstly, to the use of a nanodiamond for generating free radicals for therapeutic and/or diagnostic purposes. According to one particular implementation of the invention, heat production is coupled to the production of free radicals. The use of a nanodiamond as a medicament and/or as a diagnostic tool generating free radicals follows from the properties demonstrated by the inventors and described above.

In the context of the present invention, the therapeutic action of the nanodiamonds is because of the damage caused, directly or indirectly, by the free radicals generated at the surface of the nanodiamonds, to the molecules located immediately around the nanoparticles, and in particular less than 10 nm from the surface of the nanoparticles. In the applications aimed at cell destruction, it is therefore preferable for the nanoparticles to penetrate the cells, so that the free radicals cause damage to the cell nucleic acids (nuclear DNA and RNA and/or cytoplasmic RNAs and/or mitochondrial DNA, etc.). For this, nanodiamonds of which the average diameter is less than 100 nm, or even less than 50 nm or even less than 10 nm, are preferred for implementing the invention.

The inventors have observed that nanodiamonds which have undergone a particular surface treatment in order to create $CH_x$ functions (x=1, 2 or 3) and/or carbon in graphite form at the surface (by hydrogen plasma, high-temperature annealing under vacuum or under hydrogen for example) are particularly effective. The expression "graphitized nanodiamond" denotes herein any nanodiamond containing, at the surface, $sp^2$ hybridized carbon atoms. Of course, the presence of $sp^2$ hybridized carbon atoms at the surface of the nanodiamond does not exclude the presence of other chemical groups at the surface of these nanodiamonds. Likewise, the expression "hydrogenated nanodiamond" denotes any nanodiamond containing functions of C—H, $CH_2$ or $CH_3$ type at the surface. When nanodiamonds of which the surface has been (partially or totally) graphitized and/or hydrogenated are exposed to air or dispersed in an aqueous medium, they exhibit surface conduction properties which give them a negative electron affinity. In parallel, their surface becomes favorable to the preferential adsorption of the molecules which are responsible for free radicals in a biological medium ($H_2O$, $O_2$ and $NO_2$ principally), thus allowing a transfer of electrons from the nanodiamond to these molecules, which occurs spontaneously. Under ionizing radiation, this electron transfer is amplified and creates free radicals particularly effectively. In addition, the preferential adsorption of molecules such as $H_2O$, $O_2$ and $NO_2$ at the surface of these modified nanodiamonds makes it possible, by taking these molecules into the cells, to overcome one of the main causes of tumor cell radioresistance, which is the lack of oxygen in these cells (hypoxia), limiting the generation of oxygen-containing free radicals.

The nanodiamonds having $CH_x$ functions and/or carbon in graphite form at the surface have, in addition, a very high dielectric permittivity, which makes it possible to use them as a source of heat under an electromagnetic field oscillating at frequencies between 100 and $10^6$ Hz (Batsanov et al, 2012). These nanodiamonds also have infrared radiation absorption properties, like the other carbon-based nanomaterials, which also induce a release of heat (Yang et al, 2010). In order to obtain heat production by the nanodiamonds, infrared with a wavelength between 600 and 1400 nm will preferentially be used, this range corresponding to the infrared absorbed by biological tissues. The free radical-generating properties can then be coupled to hyperthermia.

According to one preferred implementation, the present invention therefore relates to a nanodiamond of which the surface has been at least partly graphitized and/or hydrogenated, for use for generating free radicals for therapeutic and/or diagnostic purposes, optionally coupled to heat. In particular, the present invention relates to a nanodiamond for use in combination with radiation, as a medicament and/or as a diagnostic tool generating free radicals.

Among the radiation capable of bringing about the generation of free radicals at the surface of the nanodiamond particles, mention may be made of ionizing radiation, among which electromagnetic waves such as X-rays, gamma-rays and ultraviolet rays, and also particulate radiation, in particular radiation consisting of protons, of hadrons or of beta ($\beta^+$ or $\beta^-$) particles. According to one preferred embodiment, the present invention therefore relates to a nanodiamond such as those described above, for use in combination with ionizing radiation, as a medicament and/or as a diagnostic tool.

Those skilled in the art will adjust the parameters of the radiation used (nature, energy, power and irradiation time) according to the depth of the tissue to be reached and to other clinical and technical parameters. Purely by way of indication, certain values are presented in table 1 below.

However, other radiation can be used, in place of or in combination with the radiation mentioned above. Among this radiation of various natures, mention may be made of visible, infrared, microwave or neutron radiation, in particular for obtaining heat production. The irradiations may be multiple, both in terms of the nature of the radiation used and in terms of the application of the radiation several times.

TABLE 1

| Nature of the radiation | Energy | Time | Penetration | Organs |
|---|---|---|---|---|
| UV | 3-120 eV | a few minutes | superficial | Skin and cavities (example: bladder) |
| X-rays | 20 to 150 keV | a few minutes | a few millimeters | Skin and cavities (example: bladder) |
| X-rays (orthovoltage) | 200 to 500 keV | a few minutes | up to 6 cm | Superficial organs, muscles |
| X-rays (megavoltage) | 1000 keV to 25 000 keV | a few minutes | Whole body | Deep organs (example: prostate) |

According to one particular implementation of the invention, at least some of the free radicals generated are oxygen-containing free radicals. The inventors have also shown that nitrogen can be adsorbed at the surface of the nanodiamonds. Thus, according to one implementation of the invention, at least some of the free radicals generated are nitrogenous free radicals.

Since free radicals cause breaks in DNA, the nanodiamonds described above have an advantageous application in the destruction of target cells such as cancer cells. According to one preferred embodiment, the present invention therefore relates to the use of a nanodiamond as described above, for treating a solid tumor, said use being based on the intrinsic property of the nanodiamond of generating free radicals under irradiation.

According to one particular implementation of the invention, the nanodiamond particles are functionalized. In particular, a nanodiamond according to the invention can be linked to a targeting molecule, by covalent or noncovalent bonding. Several techniques for grafting molecules to the surface of nanodiamonds have been described in the prior art, and those skilled in the art are able to choose, according in particular to the type of targeting molecule, the technique which is most suitable. By way of nonlimiting examples of methods for grafting targeting molecules to the surface of nanodiamonds, mention may be made of:

peptide coupling via the formation of an amide or ester function between the nanodiamond and the targeting molecule (Huang and Chang, 2004), direct coupling of the targeting molecule to the nanodiamond via the creation of a C—C bond between the two entities (Girard et al., 2011), cycloaddition coupling via the presence of carbons in the $sp^2$ or sp hybridization state on the nanodiamond and/or on the targeting molecule (Jarre et al., 2011), silanization coupling by the presence of silane functions on the surface of the nanodiamond and/or on the targeting molecule (Krüger et al., 2006), noncovalent coupling, based on electrostatic interactions and/or the formation of hydrogen bonds between the nanodiamond and the targeting molecule (Chen et al., 2010).

These couplings can be carried out either directly at the surface of the nanodiamonds, or by means of molecules grafted or adsorbed beforehand at the surface of the nanodiamonds. For the hydrogenated nanodiamonds, direct coupling via the creation of a C—C bond is the most efficient. For the graphitized nanodiamonds, coupling by cycloaddition is the most suitable.

According to one preferred embodiment of the nanodiamonds used for targeting according to the invention, the targeting is provided by at least one biological ligand recognized by a receptor overexpressed at the surface of certain cells. The biological ligands which make it possible to specifically target certain cells may be:

- peptides, for example the RGD peptide, or their derivatives or their analogs (for example: the somatostatin-analog peptide octreotate, a bombesin analog, a neurotensin analog, EGF, VIP, etc.),
- proteins, antibodies, or their derivatives or their analogs,
- sugars, in particular monosaccharides (for example: glucose, galactose, glucosamine or galactosamine), oligosaccharides, polysaccharides, or their derivatives or their analogs,
- oligonucleotides, DNA, RNA, their derivatives or their analogs,
- organic molecules (such as the bisphosphonate pamidronate or folate),
- organometallic complexes.

Their targeting activity is due to the molecular recognition of these ligands by receptors overexpressed at the surface of the cells in the area of interest. Ligands which are particularly preferred for implementing the invention are ligands of molecules that are frequently overexpressed at the surface of tumor cells. For example, peptides comprising the RGD motif, such as cyclo(RGDfK), cyclo(RGDyK) or cyclo(RGDfV), can advantageously be used. These peptides recognize $\alpha_v\beta_3$ integrin, which is overexpressed at the surface of tumor cells and of endothelial cells during tumor neoangiogenesis. The use of these ligands in the nanodiamonds according to the invention therefore makes it possible to target tumors and their vascularization, so as to destroy them through free-radical production, optionally coupled to heat production. Another preferred ligand is, for example, a peptide comprising the NGR motif described by Curnis et al. (2002), which also targets neovessels.

Of course, other molecules can be grafted to the surface of the nanodiamonds used in the context of the present invention, for example in order to increase their stability in a biological medium, or in order to perform labeling thereof (fluorophore, radioactive label, etc.) (FIG. 17).

Advantageously, the nanodiamonds according to the present invention can be monitored by imaging methods using the intrinsic luminescence of the colored centers in the nanodiamonds (N-V centers or the like) (Chang et al., 2008). Spectroscopy methods can also be used, in particular Raman spectroscopy (Chao et al., 2007). The practitioner can therefore verify the presence of the nanodiamonds in the area targeted, for example in a solid tumor, before subjecting this area to the irradiation that will lead to the generation of free radicals. This makes it possible to further reduce the side effects of the treatment.

As mentioned above, nanodiamonds are known for their ability to vectorize molecules. According to one particular embodiment, the present invention proposes to use nanodiamonds both for their vectorization properties (passive function) and for their properties of generating free radicals under irradiation (active function). The operating principle of this aspect of the invention is shown in FIG. 18. The coupling of the vectorization properties of nanodiamonds to the free-radical-generating properties thereof is particularly advantageous in the context of multimodal nanodiamond/radiosensitizing agent complexes. This is because the radiosensitizing agents enable a selective response by attacking biological pathways specific to tumor cells, while the nanodiamonds increase the amount of free radicals generated. The combination of these two components makes it possible to significantly increase the effectiveness and the selectivity compared with the isolated use of nanoparticles or of radiosensitizing molecules: firstly, the use of nanodiamonds makes it possible to transport the radiosensitizing agents into tumor cells in a targeted manner and to gradually release them in these cells, so that the bioavailability of the radiosensitizing agents is improved, and, secondly, the radiosensitizing agents will inactivate the defenses of the tumor cells, and therefore the radicals generated by the nanodiamonds will cause more DNA breaks in the tumor cells. This coupling makes it possible, a priori, to increase the concentrations of radiosensitizing agents delivered into tumor cells and to reduce the dose of radiation required in order to eliminate these cells.

According to this approach, the present invention relates to a composition comprising a nanodiamond as described above, optionally functionalized with a targeting molecule, and also a radiosensitizing molecule. This radiosensitizing molecule can be bonded to said nanodiamond by covalent bonding, or simply adsorbed at its surface.

Various types of radiosensitizing molecules, also called "radiosensitizing agents", have been described and can be used to implement the present invention. In this respect, mention may in particular be made of radiosensitizing agents of chemical type, a nonexhaustive list of which comprises misonidazole, metronidazole, etanidazole, pimonidazole, phenyl-propanoids and monoiodoacetic acid. These molecules can be covalently attached to the nanodiamonds, optionally via arms which are cleavable in a cell environment, enabling the release of these molecules after the internalization of the nanodiamond. By way of example of cleavable arms, mention may be made of a PEG/polylysine polymer, a peptide arm cleaved by an enzyme overexpressed in the type of tumor targeted (for example, MMP2 or cathepsin D), or else an arm comprising a disulfide bridge, which will be cleaved by thioredoxins in the lysosomes and endosomes of the cells. Alternatively, the chemical radiosensitizing agent can be linked to the nanodiamond via weak bonds (electrostatic adsorption which is either direct, or by means of a charged polymer).

As mentioned above, a new line of research in the radiosensitization field relates to the use of nucleic acids capable of modulating the expression of certain proteins involved in DNA repair. The present invention therefore also relates to a composition comprising a nanodiamond as described above and a radiosensitizing molecule consisting of a nucleic acid molecule adsorbed at the surface of the nanodiamond. The nucleic acids which are preferred for implementing this aspect of the invention are interfering RNAs capable of inhibiting the expression of a gene responsible for DNA repair, for instance an interfering RNA which inhibits the expression of the POLQ gene.

Of course, the compositions of the invention will be advantageously used in combination with radiation, in particular as an anticancer medicament, and preferably under conditions such that the radiation induces the production, at the surface of the nanodiamonds, of free radicals and/or of heat. The term "in combination" indicates that the desired effect is obtained when the cells, tissues or organs of interest, having partly incorporated nanoparticles of the invention, are excited by the radiation. However, it is not necessary for the particles and the rays to be administered simultaneously, nor according to the same protocol.

Another particular subject of the invention lies in a method for inducing or causing the lysis or the destruction of cancer cells, in vitro, ex vivo or in vivo, which comprises bringing cancer cells into contact with one or more nanodiamonds or compositions as previously described, for a period of time sufficient to allow them to penetrate into the cancer cells and, where appropriate, to allow the release of the radiosensitizing agents, and then exposing the cells to rays as defined above, said exposure inducing the generation of free radicals and/or of heat at the surface of the nanodiamonds and causing the lysis or the death of said cells. Where appropriate, an intermediate step of detecting the nanodiamonds, for example by Raman spectroscopy, is carried out before the step of exposure to the rays, in order to verify the location of the nanodiamonds.

The invention also relates to a method for treating cancer, comprising the administration, to a patient suffering from cancer, of a composition comprising nanodiamonds as previously defined, preferably functionalized with a targeting molecule, under conditions which allow the nanodiamonds or nanoparticulate aggregates to penetrate into the cancer cells, and the subsequent treatment of the patient in the presence of an excitation source, for example chosen from X-rays, gamma-rays, UV rays, protons and hadrons, resulting in a modification, a disruption or a functional destruction of cancer cells in the patient, thus treating the cancer.

The term "treatment" denotes herein any improvement in clinical signs, such as, in particular, a decrease in the size or of the development of a tumor or of a pathological tissue area, the suppression or the destruction of pathological cells or tissues, a slowing down of the progression of the pathological condition, a reduction in the formation of metastases, a regression or a complete remission, etc. The nanodiamonds and compositions of the invention can also be used in vitro or ex vivo.

The invention is usable for treating any type of cancer, in particular metastasized or non-metastasized solid tumors, for example chosen from lung, liver, kidney, bladder, breast, head-and-neck, brain, ovarian, prostate, skin, intestinal, colon, etc., cancers. The rays can be applied at any time after the administration of the particles, on one or more occasions, using any radiotherapy or radiography system already available. The nanodiamonds and compositions of the invention can be administered via various routes, preferably by systemic or local injection, or orally. Repeated injections or administrations can be envisioned, if necessary.

BRIEF DESCRIPTION OF THE DRAWINGS

The following examples and the appended figures illustrate the invention without, however, limiting the scope thereof.

Figure Legends

DETAILED DESCRIPTION

Examples

Example 1: Production of Nanodiamonds (NDs) Having Graphitic Surface Reconstructions or Surface Hydrogenated Functions The NDs having properties that are of use for the radiosensitization of tumor cells were modified using particular treatments allowing the formation of graphitic reconstructions (graphitization) or of hydrogenated functions of $CH_x$ type with x=1, 2 or 3 (hydrogenation). NDs comprising a combination of these two types of surface end groups can also be used in the context of the present invention. The methods described below are those used by the inventors for the hydrogenation (by microwave-assisted hydrogen plasma) and the graphitization (by annealing under vacuum at high temperature or by exposure to microwaves, under vacuum, of hydrogenated NDs), but these particular surface end groups can, a priori, also be obtained by other methods. It should be noted that the conditions set out are to be adapted according to the initial surface chemistry of the NDs, which can vary from one nanodiamond supplier to another. The treatments described herein were optimized for detonation NDs produced by the Nanocarbon Institute in Japan (Professor Eiji Osawa).

1.1. Hydrogenation by Microwave-Assisted Hydrogen Plasma 1.1.1. Procedure

Figure 1:
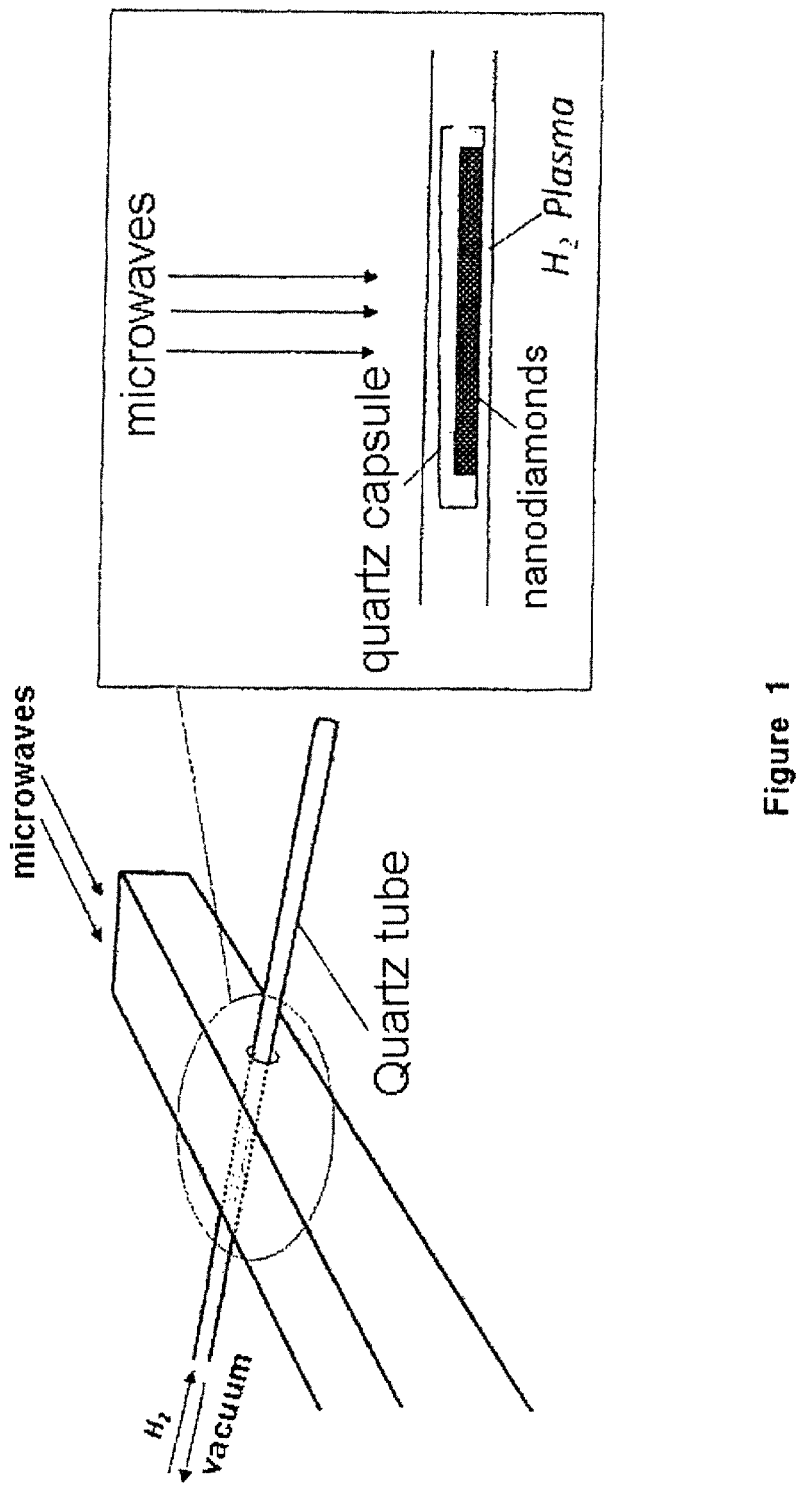
FIG. 1: Diagram of the scheme for hydrogenation of the nanodiamonds (NDs) by microwave-assisted hydrogen ($H_2$) plasma.

The method used to confer hydrogenated end groups on the NDs is described in the reference Girard et al., 2010. The NDs (approximately 50-100 mg) are introduced, via the dry route, into a quartz cartridge, or else directly into a quartz tube, which is inserted perpendicularly into a waveguide connected to a 2.45 GHz microwave generator (Sairem), as represented in FIG. 1. The waveguide is cooled with water and the tube is cooled with compressed air. This tube is connected to a device for primary pumping and for supplying high purity N9.0 hydrogen and argon gas.

Firstly, a series of purges are carried out via primary pumping in the tube (pressure<0.1 mbar) and repressurization with high purity hydrogen, then the high purity hydrogen is injected until a pressure stabilized at 12 mbar is reached. This pressure is either maintained throughout the hydrogenation process by isolation of the tube (static mode), or maintained by the combination of a continuous stream of hydrogen and a valve for pressure regulation under instruction (dynamic mode). A microwave power of 300 W is used to induce the creation of a plasma in the tube. The geometry of the microwaves in the waveguide is adjusted so as to obtain a maximum power absorbed by the plasma and a zero reflected power at the level of the generator. The tube is regularly manually turned and moved translationally in order to ensure that the majority of the NDs are exposed to the plasma. The normal exposure time is 20-30 min. In order to obtain complete hydrogenation, it is important to perform a purge after 5 min of treatment in order to discharge oxidized species desorbed from the surface of the NDs; after interruption of the microwaves, the tube undergoes primary vacuum pumping, and then pure hydrogen is reintroduced into the tube in order to again initiate the formation of a plasma. This intermediate purge is not needed in the case of a hydrogenation under a dynamic hydrogen stream. At the end of the treatment, the tube is cooled under hydrogen until it is at ambient temperature, and then the residual gas is pumped. The tube is placed at ambient temperature again by introducing argon, then the NDs can be recovered.

1.1.2. Characterization

Detailed characterizations of the surface properties of the hydrogenated NDs prepared in this way have been published (Girard et al., 2010; Girard et al., 2011; Arnault et al., 2011). The surface chemistry is studied therein by electron (XPS), infrared (FTIR) and Raman spectroscopies. In addition, three graftings, the selectivity of which on hydrogenated diamond films is known, were applied to these hydrogenated nanodiamonds; an equivalent selectivity with respect to the presence of the hydrogenated end groups of the nanodiamonds was demonstrated. This shows in particular that these NDs have negative electron affinity properties (Girard et al., 2011). These properties are responsible for their use to generate free radicals in water (see example 2).

1.2. Graphitization of Hydrogenated NDs by Microwave Exposure

The NDs hydrogenated according to the process described above can be graphitized following their hydrogenation, in situ, by simple reexposure to microwaves under primary vacuum. This is because inventors have observed that the hydrogenated NDs have the ability to absorb microwaves under vacuum. Thus, by adjusting the geometry of the microwave cavity, most of the microwave power (the inventors used 300 W for 100 mg of NDs) is absorbed by the NDs and is converted into heat. An exposure of a few seconds is sufficient to allow a very rapid increase in the temperature of the NDs, inducing the formation of surface graphitic reconstructions, as occurs in a conventional graphitization process by high-temperature annealing (see below). An exposure of more than one minute, on the other hand, results in the formation of entirely graphitic nanoparticles where the diamond core has completely disappeared. This method can be an alternative to high-temperature annealings under vacuum, the experimental protocol of which is described in detail in the section which follows.

1.3. Surface Graphitization of the Nanodiamonds by Annealing Under Vacuum 1.3.1. Procedure The surface of the nanodiamonds can be graphitized by annealing under vacuum at high temperature (between 700° C. and 900° C.) (Petit et al., 2011). These annealings under vacuum are carried out in a dedicated metal-walled chamber equipped with a silicon carbide heating element which makes it possible to achieve temperatures above 1000° C. and a combined system of primary and turbomolecular pumping which makes it possible to obtain a secondary vacuum in the chamber (of about $10^{-7}$ mbar).

Between 50 and 100 mg of dry-route NDs are placed in an alumina crucible with a lid made of the same material, which is then placed on the heating element inside the chamber. During the annealing, the temperature of the crucible is measured using an infrared camera (FLIR SC300) precalibrated according to the emissivity of the crucible, while the temperature of the heating element is estimated with a thermocouple. The chamber is then pumped at ambient temperature until a pressure of less than $5\times10^{-7}$ mbar is obtained, then the temperature of the heating element is gradually increased up to 1000° C. (corresponding to 750° C. for the crucible), while maintaining the pressure in the chamber below $5\times10^{-6}$ mbar. Once the temperature has stabilized, the crucible is left at constant temperature for a predetermined time, then the temperature of the heating element is gradually reduced to ambient temperature. The crucible is then cooled under vacuum. Once it has been brought back to ambient temperature, the chamber of the reactor is again placed under atmospheric pressure under air, making it possible to remove the crucible. The NDs can then be recovered so as to be resuspended.

1.3.2. Characterizations

Typically, an annealing at 750° C. for one hour is sufficient to obtain the formation of surface graphitic reconstructions, but longer annealings can be used to increase the degree of coverage of the surface with these graphitic reconstructions. Temperatures above 900° C. induce graphitization of the diamond core, limited graphitization at the surface of the NDs is therefore difficult to control above 900° C.

Figure 2:
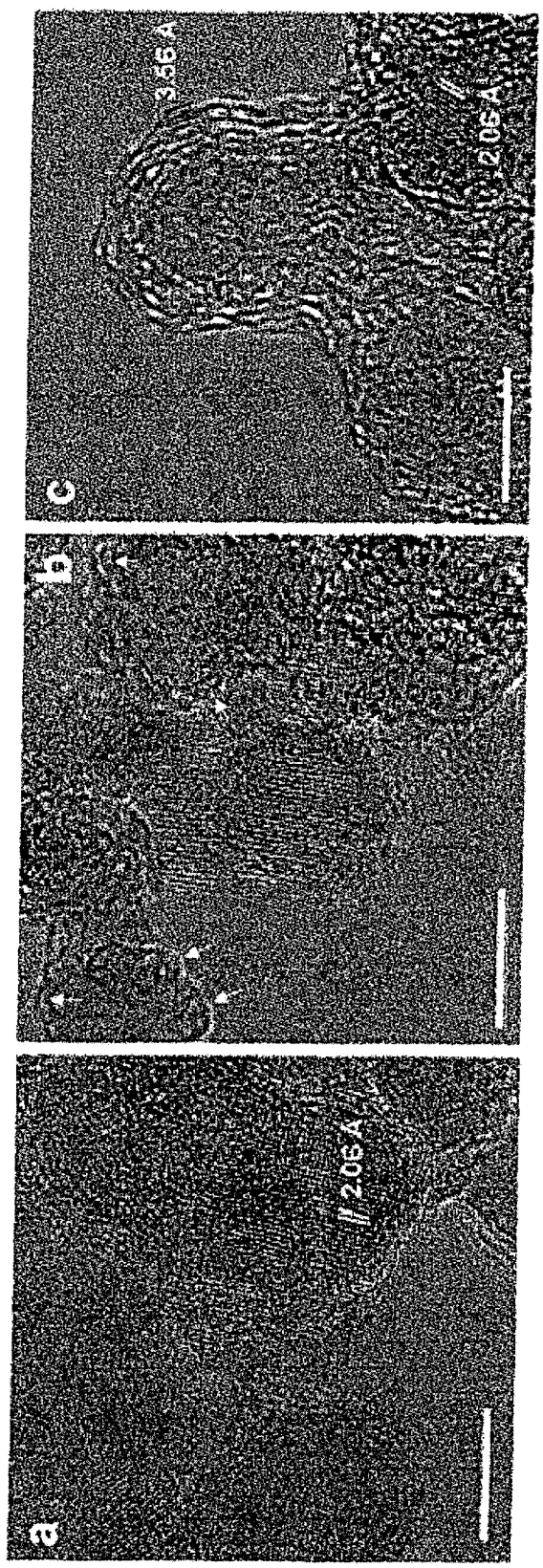
FIG. 2: High-resolution transmission electron microscopy (HRTEM) images of initial NDs (a), and NDs after 1 h (b) and 8*h* (c) of annealing under vacuum at 750° C. The diamond planes (111) and graphitic planes (001) are indicated by the white and gray lines, respectively. The graphitic surface reconstructions are indicated by white arrows. The scale bar is 5 nm.
Figure 3:
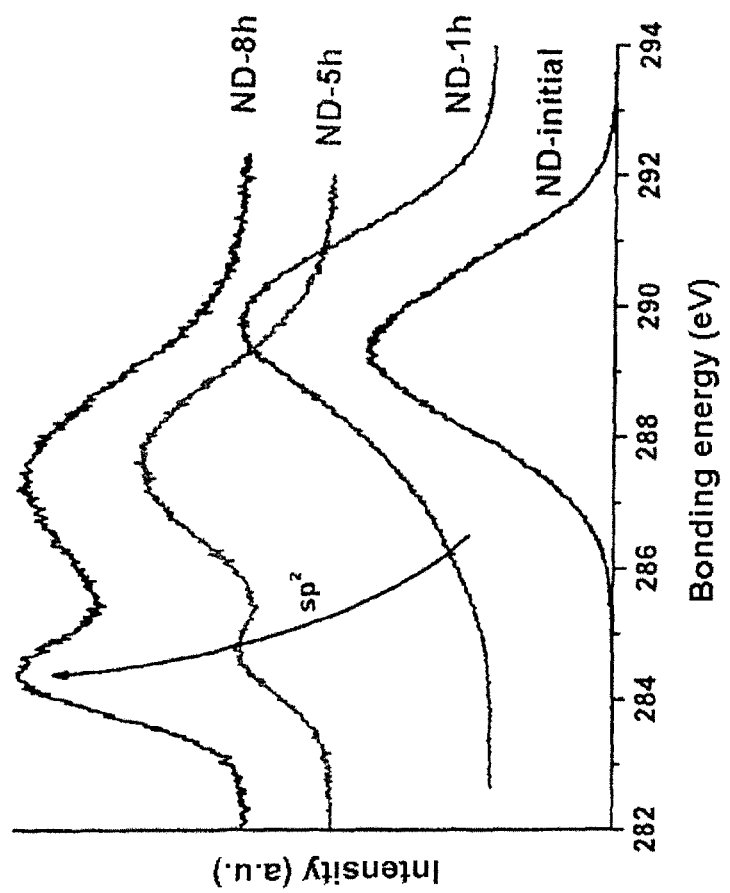
FIG. 3: X-ray photoelectron spectroscopy (XPS) spectra of the carbon core level (C1s) of the initial NDs (ND-initial), and NDs after 1 h (ND-1 h), 5 h (ND-5 h) and 8 h (ND-8 h) of annealing under vacuum at 750° C.

The graphitization of the NDs is validated by high-resolution transmission electronmicroscopy (HRTEM) after 1 h and 8 h of annealing under vacuum at 750° C., corresponding to the temperature of the crucible (FIG. 2). The images make it possible to observe the modifications of the atomic structure that are induced by the annealings. This graphitization is also validated by the analysis of the surface chemistry by X-ray photoelectron spectroscopy (XPS). Indeed, a component bonded to the $sp^2$ hybridized carbon appears after annealing under vacuum at low bonding energy compared with the $sp^3$ hybridized carbon (FIG. 3).

Example 2: Suspending of the Modified NDs in Water

The hydrogenated and/or graphitized NDs are then placed in colloidal suspension in ultrapure water (18.2 MΩ·cm at 25° C.) using a 300 W sonification immersion probe (Hielscher UP400S) operating at a frequency of 24 kHz. The NDs are initially placed in a solution of ultrapure water at a concentration of about 5 to 10 mg/ml and are then exposed to ultrasound for a minimum of 2 h. Following the sonification process, and in order to separate the largest nondispersible aggregates from the suspension, the suspensions are centrifuged at 4800 rpm for 1 h. Only the supernatant is recovered. The hydrodynamic diameter of the NDs in suspension is measured by dynamic light scattering (DLS) using dedicated equipment. The measurement of the Zeta potential characteristic of the surface charge of the nanodiamonds in solution is carried out on the same equipment (Nanosizer ZS, Malvern) with an added automatic titration module (MPT-2, Malvern) in order to carry out measurements as a function of the pH.

Figure 4:
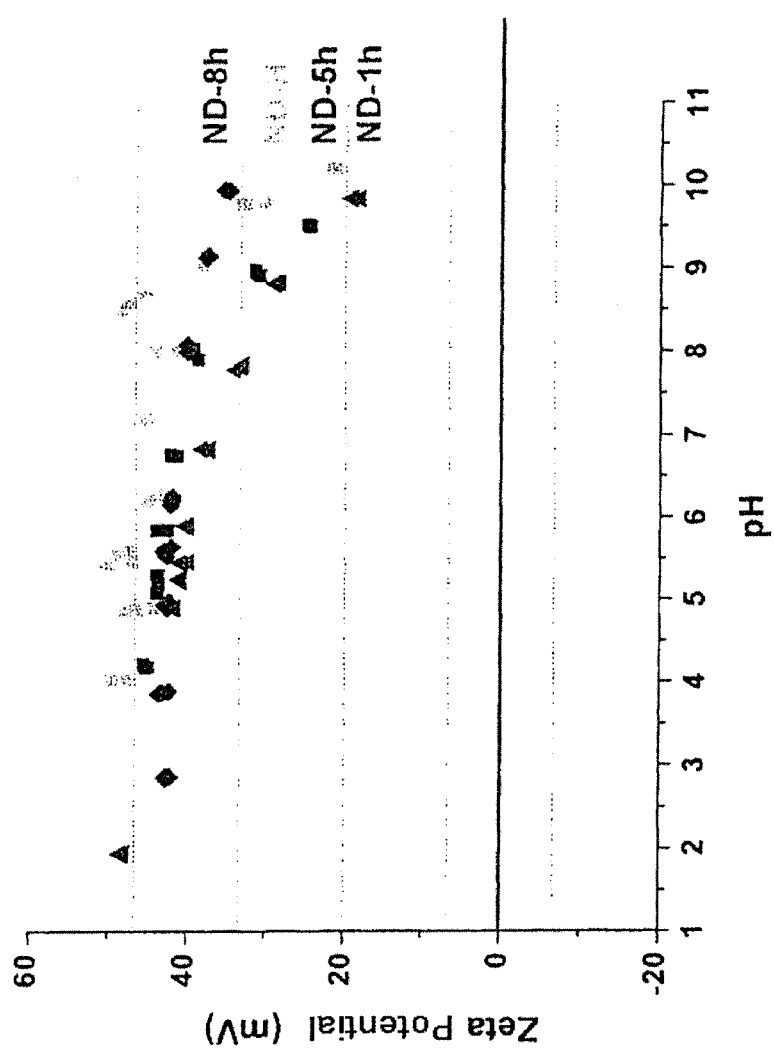
FIG. 4: Evolution of the Zeta potential of the ND-1 h, ND-5 h, ND-8 h and hydrogenated NDs (ND-H) in ultrapure water as a function of the pH.

The resulting suspensions consist of aggregates of NDs of which the hydrodynamic diameter is less than 50 nm and which have a positive Zeta potential in ultrapure water over a wide pH range, as indicated for NDs annealed under vacuum for 1 h (ND-1 h), 5 h (ND-5 h) and 8 h (ND-8 h) in FIG. 4. A similar evolution of the surface charge is observed on the hydrogenated NDs. In particular, the high Zeta potential at physiological pH makes it possible to ensure good colloidal stability of the modified NDs in this pH range.

Figure 5:
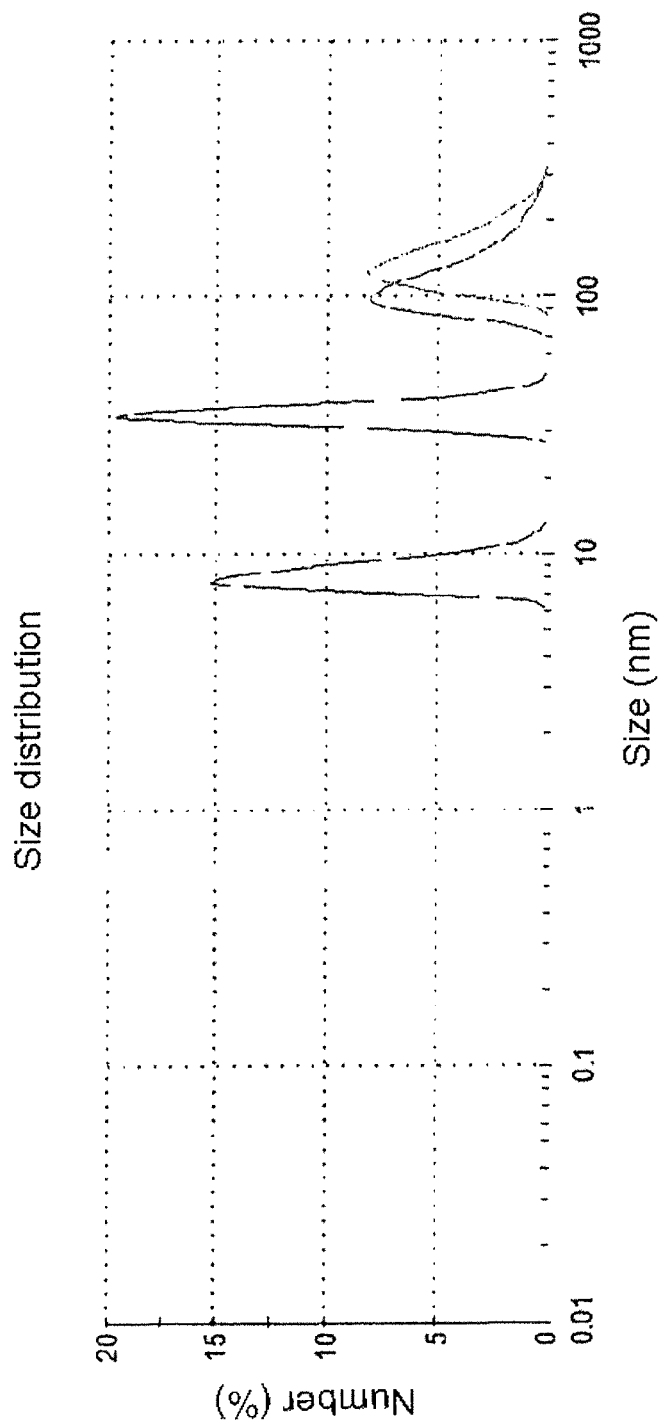
FIG. 5: Size distribution of the proteins of the DMEM medium+10% fetal calf serum (FCS) (black), and of the NDs-5 h in deionized water (blue) and in MEM just after addition (green) and after 5 h (red). The measurements are carried out at 37° C.

These NDs are stable for several months in water, but also in biological medium, as illustrated by the evolution in the hydrodynamic diameter of the NDs-5 h in a medium consisting of MEM (minimum essential medium) and 10% fetal calf serum, measured by DLS (FIG. 5). After more than 6 months in water, an average diameter of 35 nm is detected for the NDs-5 h. After addition to the [MEM+serum] medium at a concentration of approximately 0.5 mg/ml, the diameter increases to 144 nm, which is attributed to the adsorption of negatively charged serum proteins on the positive surface of the NDs. After incubation for 5 h at 37° C., the diameter is reduced to 121 nm, which shows that there is no significant effect of aggregation over time in biological medium.

Example 3: Generation of Free Radicals from the Hydrogenated (NDs-H)/Graphitized (NDs-G) Nanodiamonds (NDs)

The effect of amplification of the generation of free radicals in the vicinity of the NDs-H/G is based on two physical properties: the high density of carbon atoms (about 10 000 atoms for a nanodiamond 5 nm in diameter) in the NDs, making it possible to efficiently absorb radiation, and their ability to efficiently transfer the electrons from the diamond core to oxygen-containing species attached at the periphery of the NDs.

Figure 6:
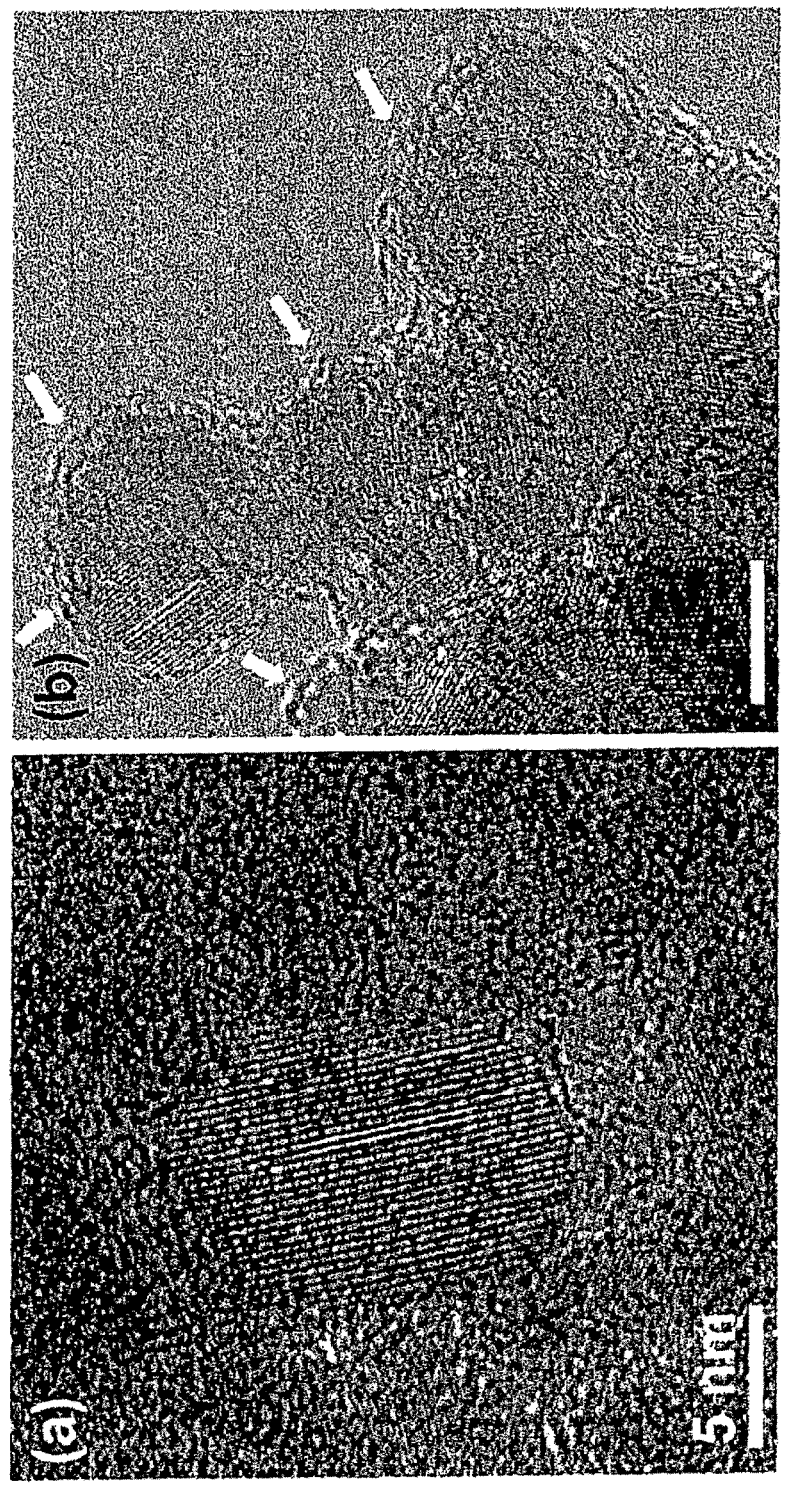
FIG. 6: HRTEM image of nanodiamonds which are hydrogenated (a) and graphitized at the surface (b). The planes (111) of the diamond are highlighted in the plane and the surface graphitic reconstructions are indicated by the white arrows. The scale bar is 5 nm.

The absorption of ionizing radiation is much greater in the NDs than in the surrounding tissues because of the high atomic density of diamond ($\approx 1.8 \times 10^{23}$ at·$cm^3$). Indeed, the distance between two atomic planes of orientation (111) of the diamond mesh is 0.206 nm, as illustrated by the high-resolution transmission electron microscopy (HRTEM) image presented in FIG. 6. Under radiation, a high concentration of secondary electrons and photoelectrons is created and they are released locally at the surface of the NDs. Indeed, the surface of the NDs-H and NDs-G behaves respectively like the surface of hydrogenated diamond films or that of a graphene plane. These two surfaces are known to allow very efficient electron transfer to surface-adsorbed molecules (Chakrapani et al., 2007; Ryu et al., 2010).

Figure 7:
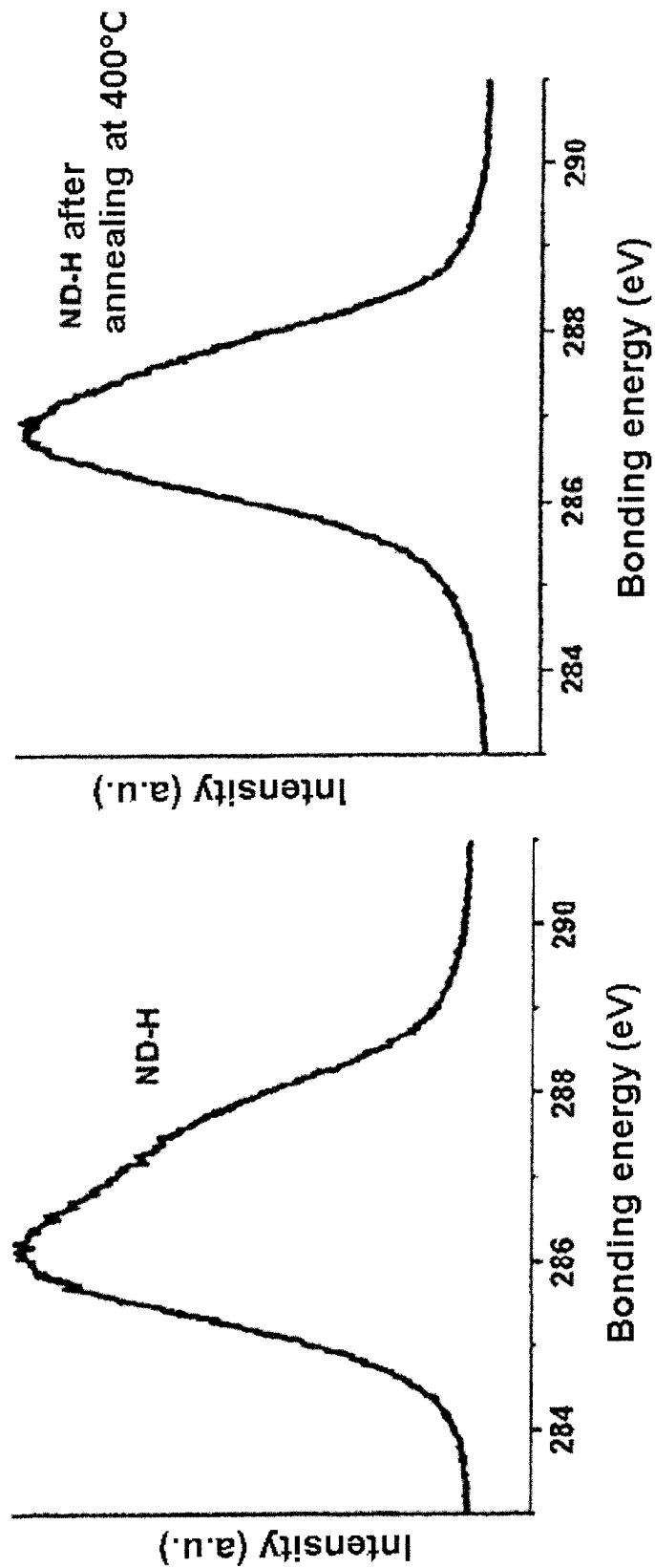
FIG. 7: XPS spectra of the carbon core level (C1s) of hydrogenated nanodiamonds after dispersion in water (a) and after 1 hour of annealing under vacuum at 400° C. (b).
Figure 8:
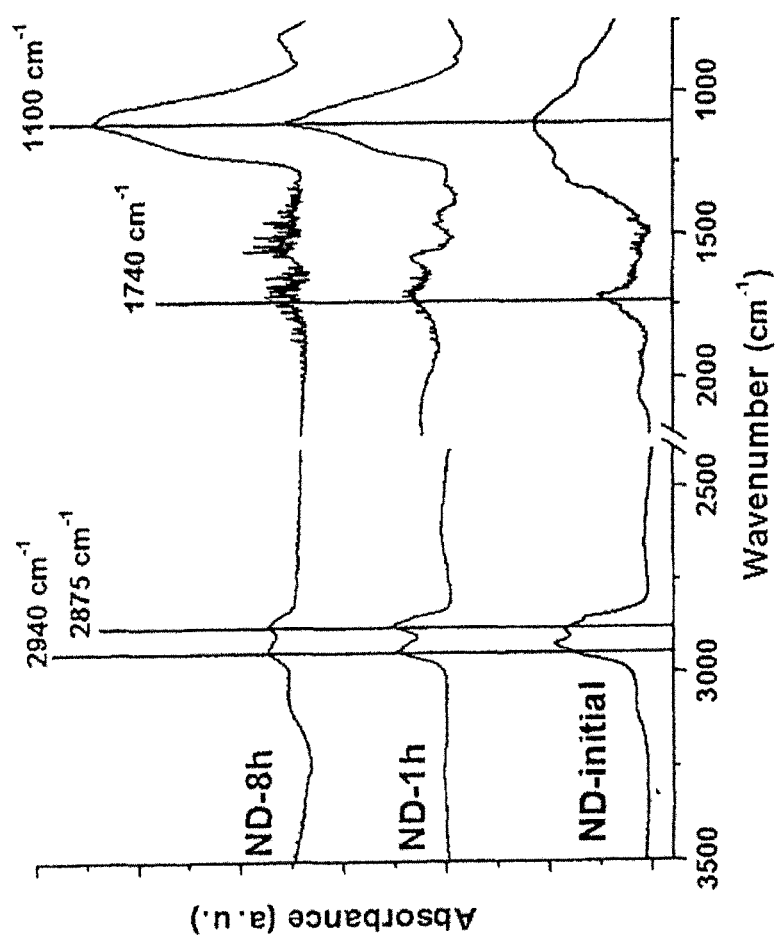
FIG. 8: Fourier transform infrared (FTIR) spectroscopy spectra of initial NDs (ND-initial), and NDs-G after 1 h (ND-1 h) and 8 h (ND-8 h) of annealing under vacuum.

In parallel, the NDs-H and NDs-G have the possibility of efficiently adsorbing oxygen-containing species at their surface. Thus, a high concentration of oxygen was measured at the surface of the NDs-H and NDs-G, representing up to 6 atm. % according to the XPS spectra, after dispersion in ultrapure water. The oxygen comes from adsorption, via noncovalent bonds, of water ($H_2O$) and dioxygen ($O_2$) molecules and also from single-bond C—O covalent bonds which can be bonded to hydroxyl, ether, epoxide or endoperoxide functions. This oxygen, covalently bonded to the surface of the NDs, is characterized by the presence of a high-energy shoulder of bonding on the C1s carbon core level spectra using X-ray electron spectroscopy (XPS) presented in FIG. 7a. On the other hand, this oxygen is weakly bonded since annealing under vacuum at 400° C. makes it possible to desorb most of this oxygen (FIG. 7b). Using infrared spectroscopy (FTIR), after desorption of the species adsorbed noncovalently by annealing under vacuum at 200° C., a significant band at 1100 $cm^{-1}$ was observed, which may be linked to functions of ether, epoxide or endoperoxide type (FIG. 8), validating the results obtained by XPS.

Thus, the electrons generated by irradiation are transferred to these molecules adsorbed onto the surface of the NDs. Since these molecules are precursors of oxygen-containing free radicals ($O_2$, HO, $H_2O_2$, etc.), the transfer of electrons coming from the NDs induces a strong production of free radicals at the surface of the NDs. It should be noted that nitrogen was also measured by XPS; it is therefore possible that nitrogenous molecules are also adsorbed at the surface of the NDs, implying the generation of nitrogenous free radicals.

The adsorption of oxygen on the surface induces a positive Zeta potential of the NDs-H and NDs-G, ensuring good colloidal stability by electrostatic stabilization, even in biological medium. The biological environment which contains the NDs is therefore directly exposed to the free radicals generated at the surface of the NDs.

Example 4: Cell Index and Oxidative Stress Measured in the Caki-1 Tumor Line, Under Gamma-Irradiation in the Presence of NDs-COOH and NDs-H The radiosensitizing effect of the nanodiamonds was studied on a kidney tumor line Caki-1, known to be particularly radioresistant. Cells exposed to NDs-COOH and NDs-H at three concentrations (10, 100 and 500 µg/ml), and also cells without NDs, were subjected to a radiation of 4 Gray (Gy).

The evolution of the cell index, characteristic of the overall response of the cells (morphology, adhesion, viability, etc.), was monitored in real time over the course of 120 h after irradiation by impedancemetry using the xCELLigence system (Roche).

The oxidative stress was then evaluated by observing the cells by optical microscopy and quantified by flow cytometry.

4.1. Results on the NDs-COOH

Figure 9:
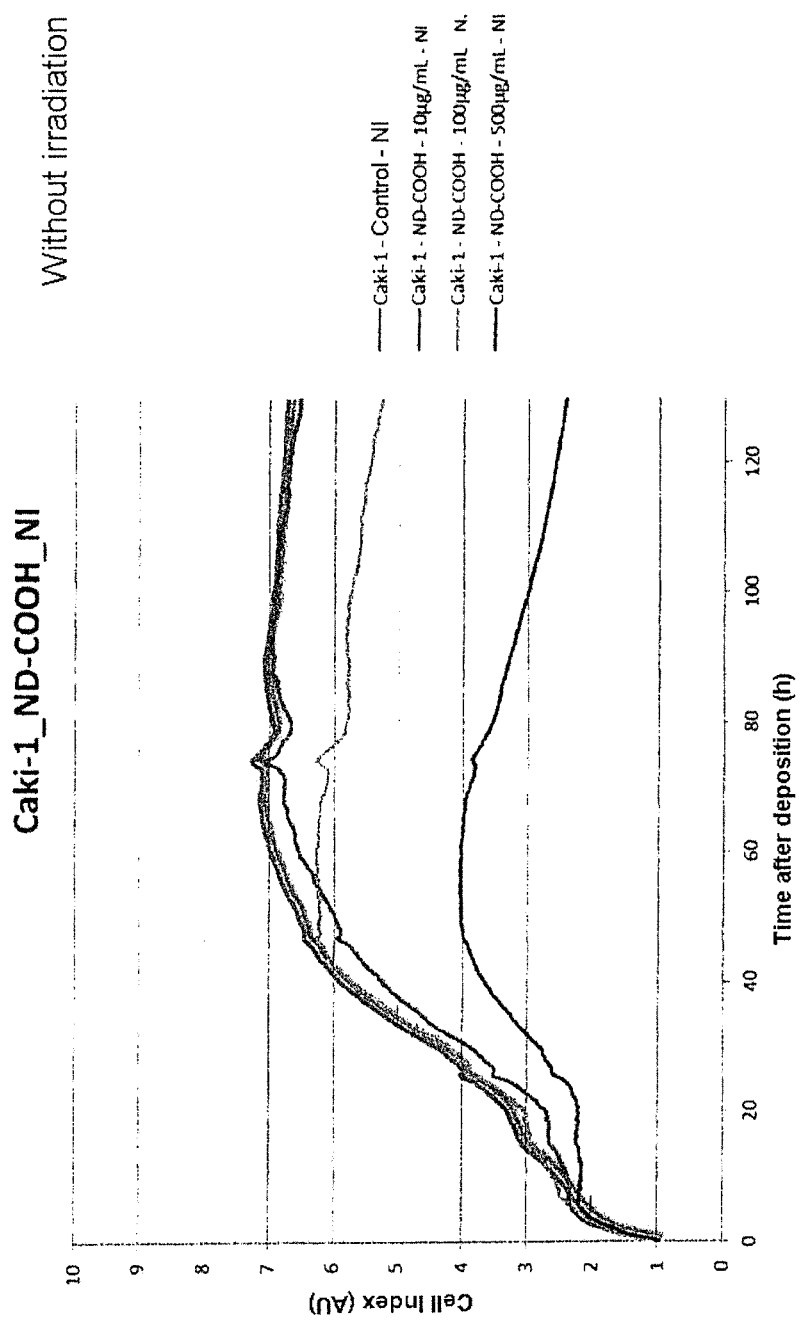
FIG. 9: Cell response of the Caki-1 line after exposure to NDs-COOH without irradiation.

After exposure to the NDs-COOH, the cell index evolves in an equivalent manner up to 48 h for the concentrations of 10 and 100 µg/ml (FIG. 9). A very small decrease is observed at 100 µg/ml for longer times. On the other hand, the cell index is greatly decreased for the 500 µg/ml concentration.

These results show that the NDs-COOH are not toxic for concentrations below 100 µg/ml, but that a certain toxicity can be observed at higher concentration. The toxicity is therefore dose-dependent.

Figure 10:
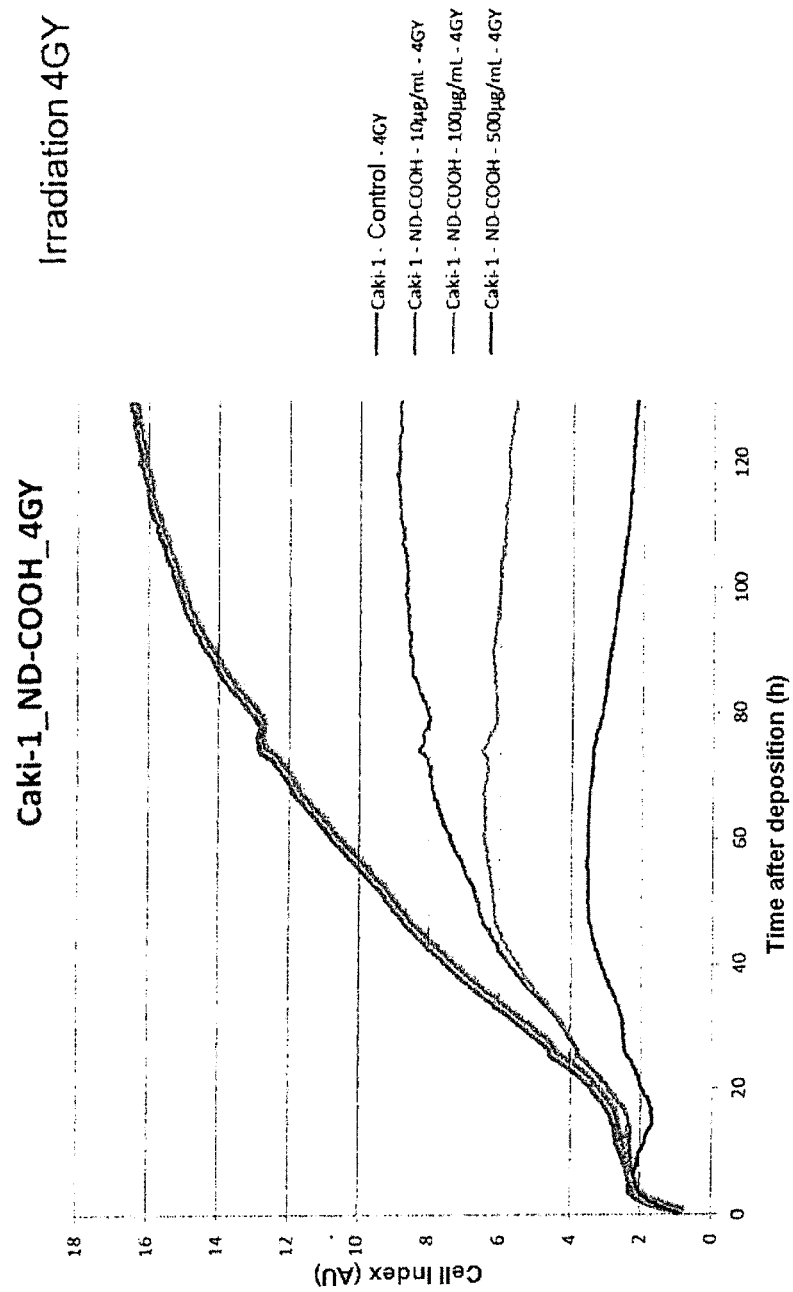
FIG. 10: Cell response of the Caki-1 line after exposure to NDs-COOH after an irradiation of 4 Gy.

After irradiation of 4 Gy the increase in the cell index of the control shows that this irradiation is too weak to create significant toxicity without nanoparticles (FIG. 10). On the other hand, the cell index is halved compared with the control after an exposure to the NDs-COOH at a concentration of 10 µg/ml, or even further reduced for the higher concentrations.

The NDs-COOH therefore clearly have a radiosensitizing effect, which is dependent on the dose of NDs-COOH injected into the cells. Furthermore, these NDs are not toxic at concentrations below 100 µg/ml.

4.2. Results on the NDs-H

Figure 11:
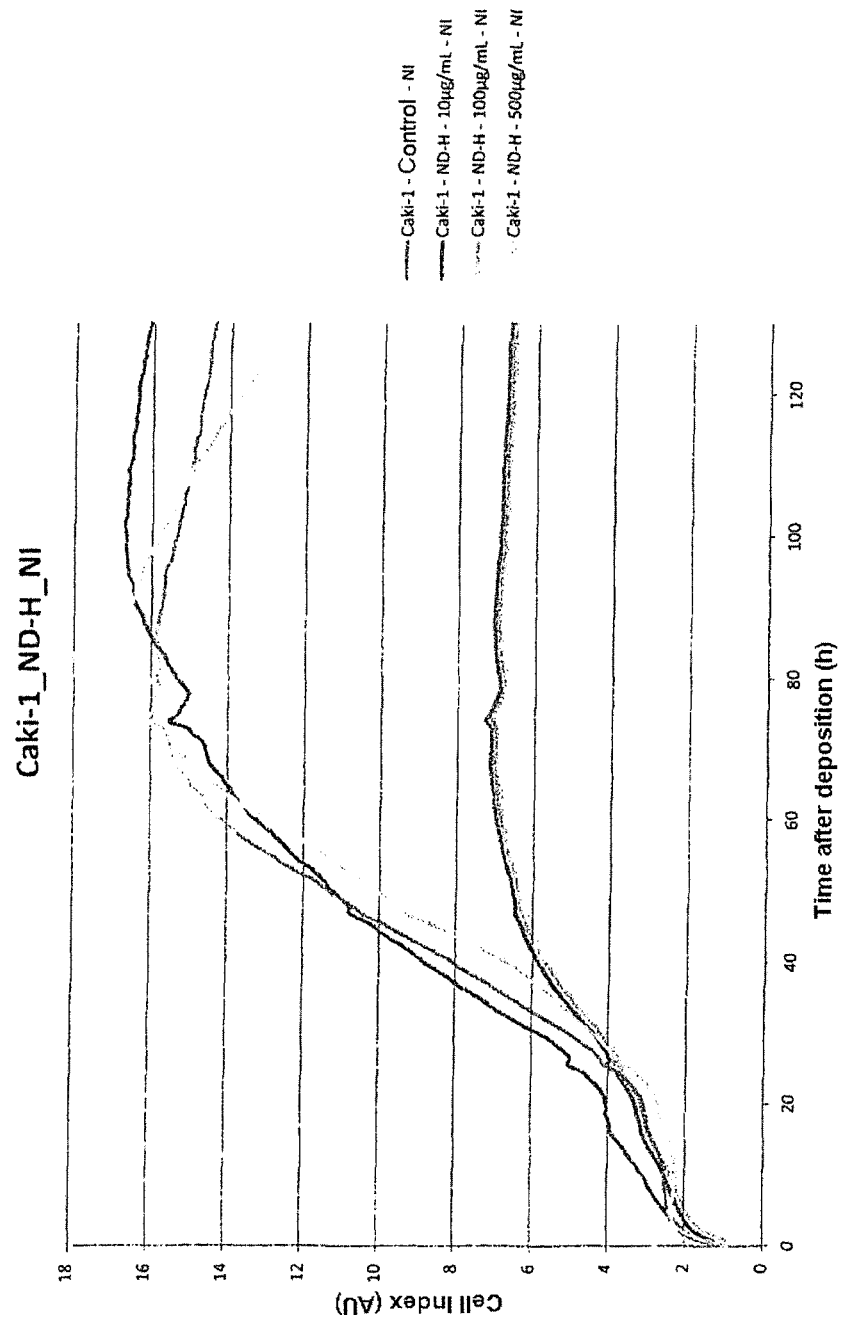
FIG. 11: Cell response of the Caki-1 line after exposure to NDs-H without irradiation.
Figure 12:
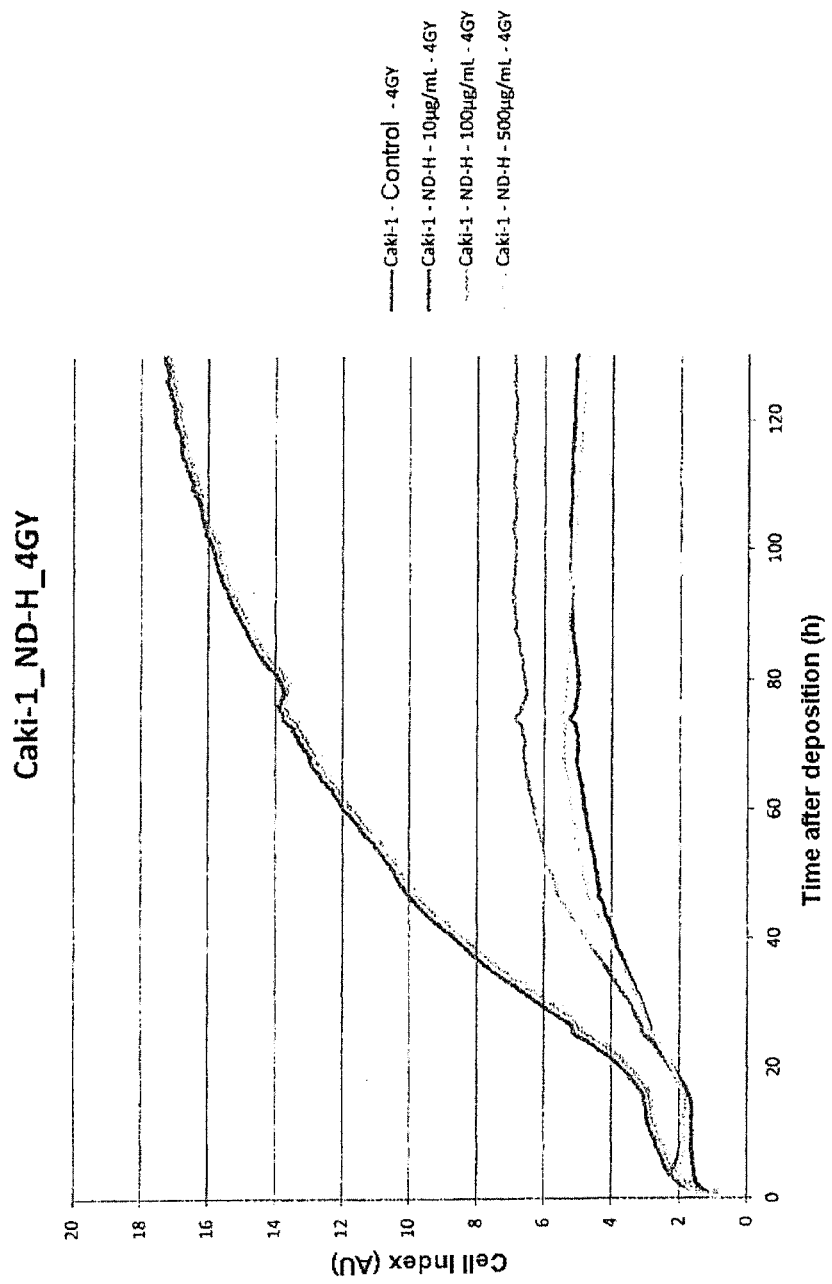
FIG. 12: Cell response of the Caki-1 line after exposure to NDs-H after an irradiation of 4 Gy.

The same protocol was applied with NDs-H (FIGS. 11 and 12). It should be noted that the toxicity of the NDs-H is even lower than the NDs-COOH since no toxicity is detected even for the concentration of 500 µg/ml, which would be reflected by a decrease in the cell index. The decrease observed after 90 h is probably due to a saturation of the signal detected by impedancemetry, due to the high concentration of NDs-H used. A significant increase in the cell index is on the other hand observed, which may result, for example, from an increase in cell size after incorporation of the NDs-H.

After irradiation, the control follows the same increase as in the previous case. On the other hand, with the presence of NDs-H, the toxicity is very significant. The cell index is thus divided by 3.4 for a concentration of 10 µg/ml. The toxicity does not appear to be dependent on the dose of NDs-H since a similar evolution of the cell index is observed at higher concentrations. This result is coherent with toxicity induced by an oxidative stress at a very low concentration of NDs-H, only under irradiation.

4.3. Results Linked to Oxidative Stress

Firstly, the oxidative stress was evaluated by observing the morphology of the cells by optical microscopy.

Figure 13:
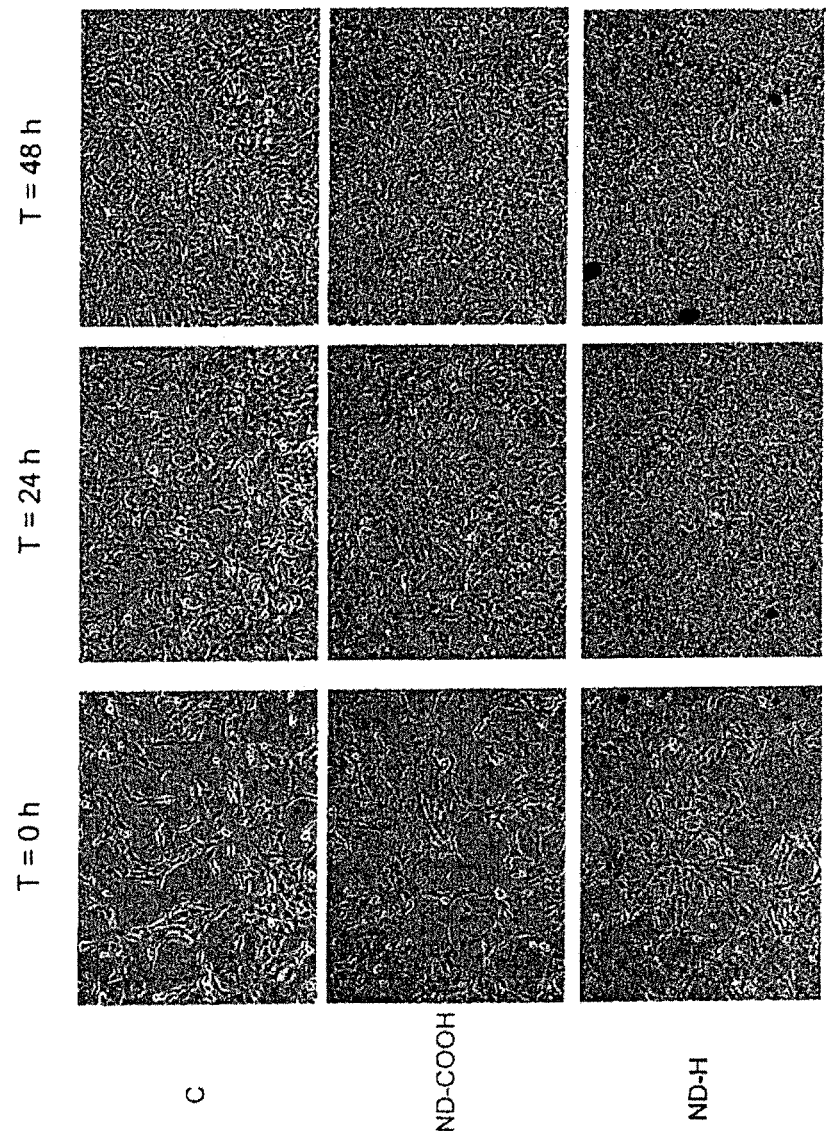
FIG. 13: Evolution of the Caki-1 cells after exposure to NDs-COOH and NDs-H, without irradiation.

There is no particular evolution at the level of the control cells without/with irradiation. After the addition of nanodiamonds, the formation of vacuoles (appearing with a blue contrast), characteristic of toxicity induced by oxidative stress, is observed (FIG. 13). The number of vacuoles increases over time.

Figure 14:
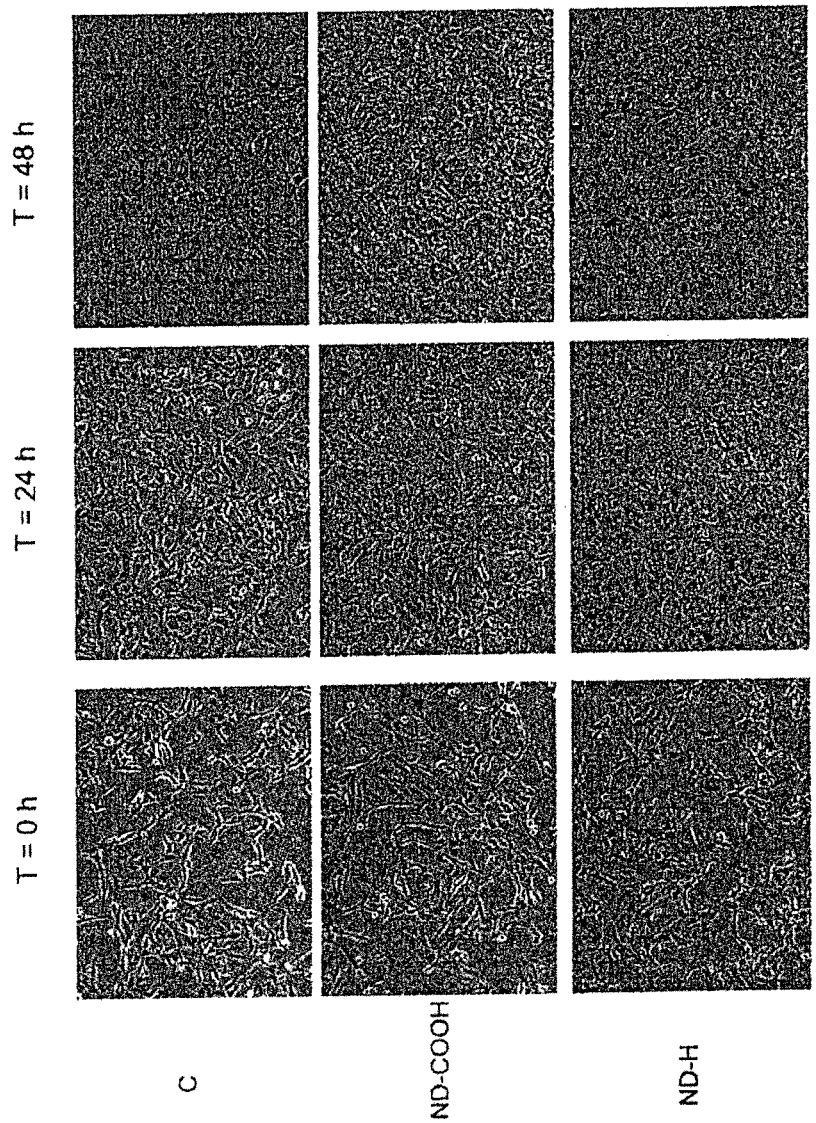
FIG. 14: Evolution of the Caki-1 cells after exposure to NDs-COOH and NDs-H, after an irradiation of 4 Gy.

The concentration of vacuoles significantly increases after irradiation in the cells exposed to the NDs (FIG. 14), which is in agreement with the previous results.

Quantitative oxidative stress measurements were carried out by measuring the fluorescence of a probe sensitive to oxygen-containing free radicals (2', 7'-dichlorofluorescein) by flow cytometry. Once exposed to the various experimental conditions (NDs-H, irradiation, NDs-H+irradiation), the cells were detached from their culture support, resuspended, and then incubated for 10 minutes in the presence of this probe. Once it has entered the cells, the probe can remain in nonfluorescent reduced form or can become oxidized and therefore emit a fluorescent signal. The intensity of fluorescence is directly linked to the amount of oxygen-containing free radicals, which allows a relative quantification regarding oxidative stress (Chen et al., 2010). This method makes it possible to measure total intracellular oxygen-containing free radicals, contrary to the measurement of oxidized proteins for example.

Figure 15:
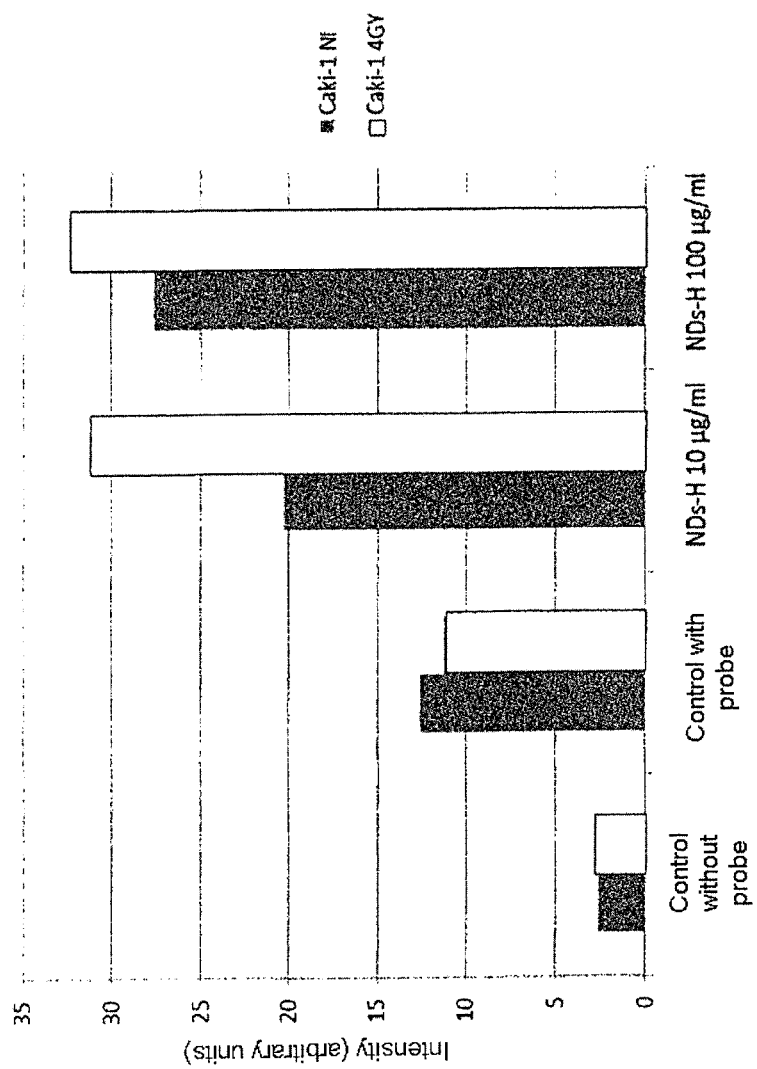
FIG. 15: Oxidative stress induced by the NDs-H with or without irradiation. The control without probe illustrates the background of luminescence which is not linked to the free radicals. The other control is exposed to the fluorescent probe but not to the NDs-H. The gray bars represent the intensity of the oxidative stress in the nonirradiated cells, and the white bars the intensity of the oxidative stress in the cells having undergone a radiation of 4 Gy, one hour after this irradiation.

The results obtained in FIG. 15 show that:
For the cells exposed to the NDs-H and not irradiated, the oxidative stress induced depends on the concentration. It is doubled for an NDs-H concentration of 100 µg/ml.
For the cells irradiated and not exposed to the NDs-H, the oxidative stress is, at 1 h after irradiation, identical to that of the cells not irradiated and not exposed to the NDs-H.
For the cells exposed to the nanoparticles and irradiated, the oxidative stress is tripled compared with the reference without NDs-H, but this increase is not dependent on the dose of NDs-H.

There is therefore a provision of free radicals in the cells after incorporation of the NDs-H, but these free radicals induce significant toxicity due to oxidative stress only after irradiation according to the evolution of the cell index. The generation of free radicals is maintained by the NDs-H since, even one hour after irradiation, the oxidative stress is higher than without irradiation, which is not the case with the control.

4.4. Conclusions

The nanodiamonds therefore have a radiosensitizing effect which makes it possible to amplify the effect of the radiation by generating a greater creation of free radicals. Simple exposure to a dose that is normally insufficient to induce the death of tumor cells makes it possible to obtain death due to oxidative stress when the cells have been preexposed to the NDs. The cells exposed to the NDs can therefore be selectively treated. The NDs are particularly advantageous since they do not generate toxicity in the absence of radiation and the nonirradiated cells will not be affected by the presence of NDs. The initial toxicity is low and the radiosensitizing effect is amplified for NDs-H, which are therefore particularly advantageous.

Example 5: Use of Hydrogenated Nanodiamonds for Vectorizing Biological Molecules into Cells In order to verify the capacity of the hydrogenated nanodiamonds (ND-H) to bind and transport molecules of biological interest into cells, ND-H particles were mixed with an equal volume of a telomeric probe consisting of peptide nucleic acid analog (PNA), labeled with the fluorophore Cy3. The final concentrations in the mixture were 64.52 µg/cm$^3$ for the NDs-H and 0.5645 µM for the PNA-Cy3 probe. The PNA-Cy3 probe was denatured by heating at 80° C. for 5 minutes, before being mixed with the NDs-H.

After incubation for 10 minutes at ambient temperature, the mixture of NDs-H and PNA-Cy3 probe was exposed to Caki-1 cells in culture (in Labtek 8-well plates). The cells were maintained in the presence of the mixture for 24 h and 72 h, under standard cell culture conditions. The cell nuclei were then labeled with the fluorescent label (Hoechst 33342), and the plates were observed directly using an inverted fluorescence microscope. For the nuclear labeling, the excitation/emission filter was 350 nm/460 nm, and for the PNA-Cy3 labeling, it was 550 nm/570 nm.

Figure 16A:
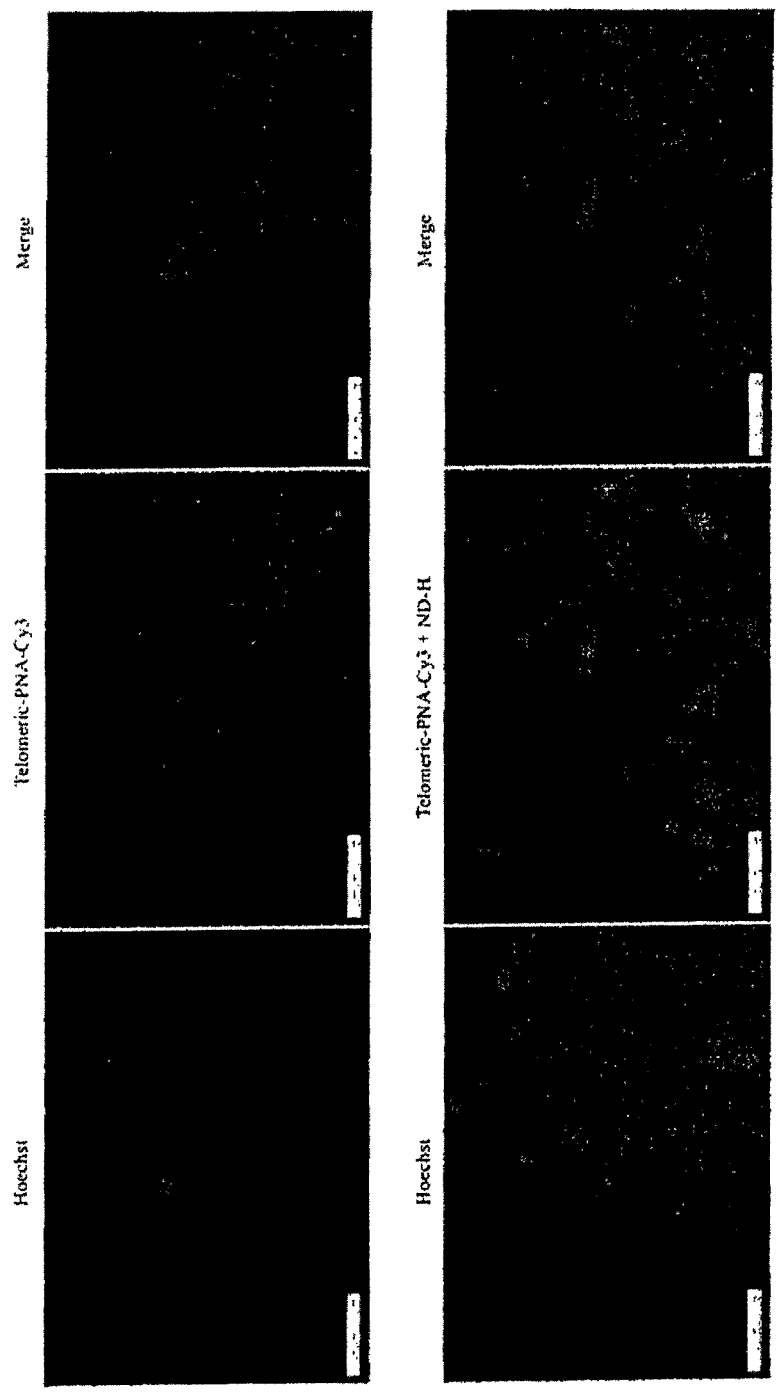
FIG. 16: Internalization of a peptide nucleic acid probe labeled with the fluorophore Cy3 (PNA-Cy3), adsorbed at the surface of ND-H. The observations were made after 24 h (A) or 72 h (B) of incubation of Caki cells in the presence of an ND-H/PNA-Cy3 mixture. The cell nuclei were labeled with bisbenzimide Hoechst 33342.
Figure 16:
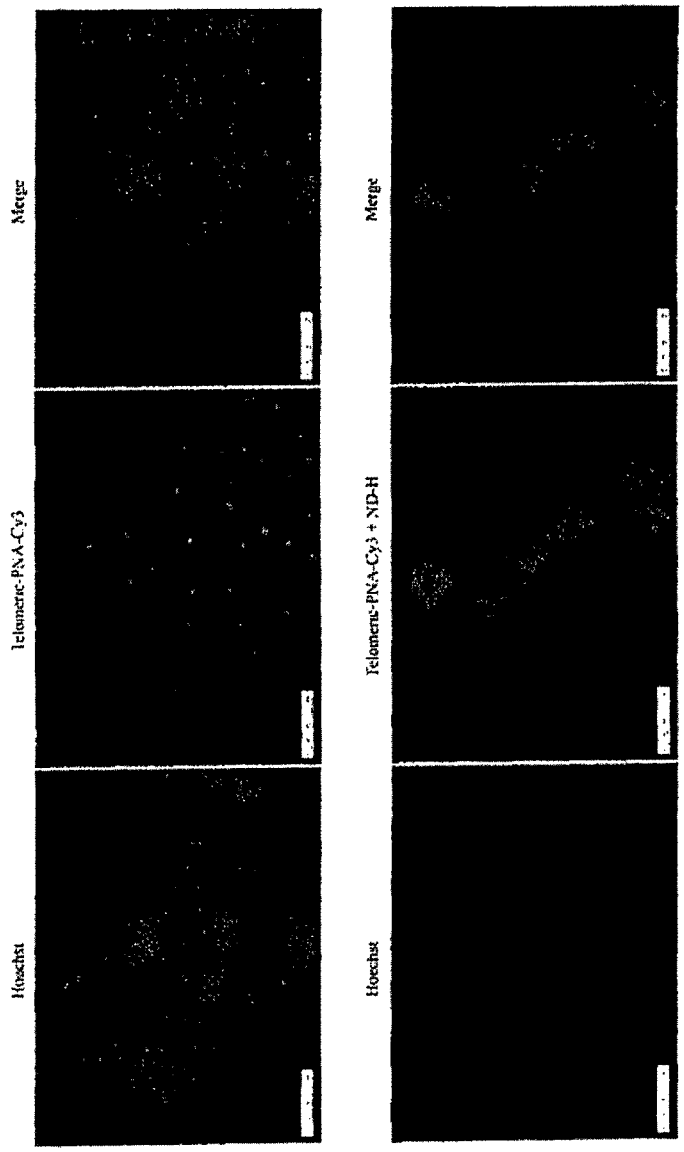
Figure 17:
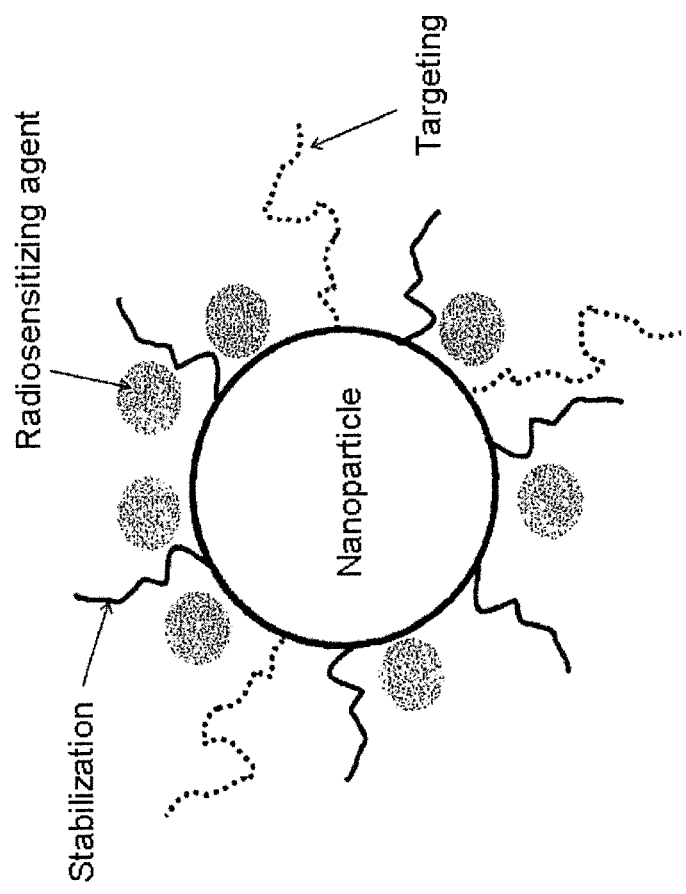
FIG. 17: Diamond nanoparticle/radiosensitizing agent complex.
Figure 18:
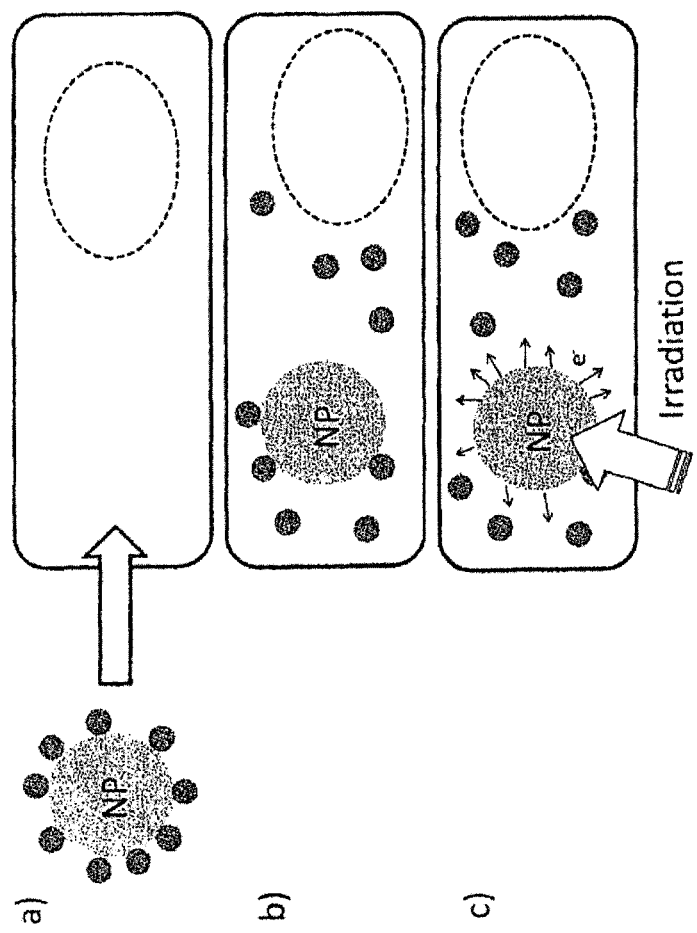
FIG. 18: Operating principle. a) Incorporation of the nanodiamond (NP)/radiosensitizing agent complex into a cell, b) release of the radiosensitizing agents and inhibition of the defenses of the cell, c) generation of electrons and formation of free radicals under irradiation.

The internalization of the PNA-Cy3 probe was observed only in the case where the ND-H particles had been mixed with this probe. In the absence of ND-H, the PNA-Cy3 probe was not internalized (FIG. 16).

These results demonstrate the capacity of the NDs-H to bind a PNA-Cy3 probe and to transport it into the cells. The molecule internalized here has no major cytotoxic activity, but it is chemically similar to cytotoxic molecules such as that used in example 6 below, which will make it possible to obtain synergy with the cytotoxic activity of the NDs-H subjected to radiation. In addition, this probe is less (negatively) charged than the cytotoxic molecules of therapeutic interest which may be used clinically. These more negatively charged molecules adsorb more easily at the surface of the NDs-H and will be more efficiently vectorized into the cells. These results therefore demonstrate the capacity of the NDs-H to vectorize, into cells, cytotoxic molecules of therapeutic interest such as nucleic acids or PNAs.

Example 6: Use of Radiosensitizing Nanodiamond/—Interfering RNA Complexes for Treating Tumors Nanodiamonds (primary size of 5 nm) are prepared so as to have a positive Zeta potential according to the processes described above. For the hydrogenated and/or graphitized NDS, a step of sonification in water makes it possible both to disperse the nanodiamonds and to efficiently adsorb molecules ($H_2O$, $O_2$ and $NO_2$ mainly) onto their surface, thus giving them a positive surface charge.

POLQ interfering RNAs, having the capacity to inhibit the messenger RNAs encoding polymerase theta, enabling DNA repair in certain tumor cells (the POLQ gene is overexpressed in the most aggressive breast cancers, for example), are adsorbed onto the surface of the nanodiamonds. The RNAs, which have a negative surface charge, can be adsorbed by electrostatic interaction onto the surface of the positively charged nanodiamonds by simple addition of the RNAs to the nanodiamond suspension.

These nanodiamond/RNA complexes are then injected into tumor cells, where they preferentially enter due to the increased permeability of tumor cell membranes. The POLQ interfering RNAs are gradually released in the tumor cells and inhibit polymerase theta synthesis. The tumor cells are made more sensitive to radiation.

The tumor cells are irradiated with X-rays, which leads to the release of free radicals in the cells that have internalized the nanodiamonds.

REFERENCES

Arnault, J.-C.; Petit, T.; Girard, I I.; Chavanne, A.: Gesset, C.; Sennour, M.; Chaigneau, M. Surface chemical modifications and surface reactivity of nanodiamonds hydrogenated by CVD plasma. Physical Chemistry Chemical Physics, 2011, 13, 11481-11487.

Batsanov, S. S.; Gavrilkin, S. M.; Batsanov. A. S.; Poyarkov, K. B.; Kulakova, I. I.; Johnson D. W. and Mendis B. G., Giant dielectric permittivity of detonation-produced nanodiamond is caused by water, Journal of Materials Chemistry, 2012, 22, 11166-11172.

Begg, A. C., Stewart. F. A. and Vens, C. Strategies to improve radiotherapy with targeted drugs. Nature Review Cancer. 2011, 11, 239-253.

Girard, H. A.; Arault, J. C. C.; Perruchas, S.; Saada, S.; Gacoin. T.; Boilot, J.-P. P.; Bergonzo, P. Hydrogenation of nanodiamonds using MPCVD: A new route toward organic functionalization. Diamond and Related Materials, 2010, 19, 1117-1123.

Chakrapani, J. C. Angus, A. B. Anderson, S. D. Wolter, B. R. Stoner, G. U. Sumanasekera, Charge Transfer Equilibria Between Diamond and an Aqueous Oxygen Electrochemical Redox Couple, Science. 2007, 318, 1424-30.

Chang, Y.-R.; Lee, H.-Y.: Chen, K.; Chang, C.-C.; Tsai, D.-S.; Fu, C.-C.: Lim. T.-S.; Tzeng, Y.-K.; Fang, C.-Y.; Han. C.-C.; Chang, H.-C. and Fann, W., Mass production and dynamic imaging of fluorescent nanodiamonds. Nature Nanotechnology, 2008, 3, 284-288.

Chao, J. I., Perevedentsva, E., Chung, P. H., Liu, K. K., Cheng, C. Y., Chang, C. C. and Cheng, C. L., Nanometer-sized diamond particle as a probe for biolabeling. Biophysical Journam, 2007, 93, 2199-2208 (2)

Chen M., Zhang X.-Q., Man H. B., Lam R., Chow E. K., Ho D., Nanodiamond Vectors Functionalized with Polyethylenimine for siRNA Delivery, The Journal of Physical Chemistry Letters, 2010, 1, 3167-3171.

Chen, X.; Zhong, Z.; Xu, Z.; Chen, L.; Wang Y., 2', 7'-Dichlorodihydrofl uorescein as a fluorescent probe for reactive oxygen species measurement: Forty years of application and controversy, Free Radical Research, 2010, 44 (6), 587-604.

Girard. H. A.; Petit. T.; Perruchas, S.; Gacoin, T.; Gesset, C.; Arnault, J. C.; Bergonzo, P. Surface properties of hydrogenated nanodiamonds: a chemical investigation. Physical Chemistry Chemical Physics. 2011, 13, 11517-11523.

Curnis, F., G. Arrigoni, et al., Differential binding of drugs containing the NOR motif to CD13 isoforms in tumor vessels, epithelia, and myeloid cells Cancer Research, 2002, 62(3): 867-74.

Higgins, G. S., Prevo. R., Lee, Y. F., Helleday, T., Muschel, R. J., Taylor, S., Yoshimura, M., Hickson, L. D., Bernhard, E. J. and McKenna, W. G. A small interfering RNA screen of genes involved in DNA repair identifies tumor-specific radiosensitization by POLQ knockdown. Cancer Research, 2010, 70, 2984-2993.

Huang L C, Chang I I C. Adsorption and immobilization of cytochrome c on nanodiamonds. Lungnmuir, 2004, 20 (14), 5879-84.

Jarre, G., Liang, Y., Betz. P., Lang, D. and Krueger, A., Playing the surface game-Diels-Alder reactions on diamond nanoparticles. Chemical Communication (Cambridge), 2011, 47, 544-546.

Krüger A, Liang Y, Jare G, Stegk J., Surface functionalisation of detonation nanodiamond suitable for biological applications. Journal of Material Chemistry, 2006, 11, 2322-2328.

Petit, T.; Arnault, J.-C.; Girard, H. A.; Sennour, M.; Bergonzo, P. Early stages of surface graphitization on nanodiamond probed by x-ray photoelectron spectroscopy. Physical Review B, 2011, 84, 233407.

Ryu. L. Liu. S. Berciaud, Y.-J. Yu, H. Liu, P. Kim, G. W. Flynn, L. E. Brus, Atmospheric Oxygen Binding and Hole Doping in Deformed Graphene on a SiO2 Substrate, Nano Letters, 2010, 10, 4944-4951.

Yang. K.; Zhang. S.; Zhang, G.: Sun, X.: Lee S.-T. and Liu, Z. Graphene in Mice: Ultrahigh In Vivo Tumor Uptake and Efficient Photothermal Therapy, Nano Letters, 2010, 10, 3318-3323.

The invention claimed is:

1. A method of generating free radicals for therapeutic purposes comprising a step of exposing nanodiamonds to radiation,
wherein the nanodiamonds are beforehand subjected to a graphitization, or a graphitization and a hydrogenation to have a surface that has been at least partially graphitized, or graphitized and hydrogenated, respectively.

2. The method as claimed in claim 1, wherein the generation of free radicals is coupled to heat generation.

3. The method as claimed in claim 1, wherein the nanodiamond has an average diameter that is less than 10 nm.

4. The method as claimed in claim 1, wherein oxygen-containing free radicals are generated.

5. The method as claimed in claim 1, wherein nitrogenous free radicals are generated.

6. The method as claimed in claim 1, wherein the radiation is electromagnetic radiation.

7. The method as claimed in claim 6, wherein the electromagnetic radiation consists of X-rays.

8. The method as claimed in claim 6, wherein the electromagnetic radiation consists of gamma-rays.

9. The method as claimed in claim 6, wherein the electromagnetic radiation consists of ultraviolet rays.

10. The method as claimed in claim 1, wherein the radiation is particulate radiation.

11. The method as claimed in claim 10, wherein the particulate radiation consists of protons.

12. The method as claimed in claim 10, wherein the particulate radiation consists of hadrons.

13. The method as claimed in claim 1, for use as a medicament intended for the destruction of target cells.

14. The method as claimed in claim 13, the target cells are cancer cells.

15. The method as claimed in claim 1 for use in treating a solid tumor.

16. The method as claimed in claim 1, wherein the nanodiamond is functionalized.

17. The method as claimed in claim 16, wherein the nanodiamond is bonded to a targeting molecule.

18. The method as claimed in claim 17, wherein the targeting molecule is a biological ligand recognized by a receptor overexpressed at the surface of certain cells.

19. The method as claimed in claim 18, wherein the biological ligand is chosen from the group consisting of a peptide, a protein, an antibody, a sugar, an oligonucleotide, an organic molecule, and an organometallic complex.

20. The method as claimed in claim 19, wherein the biological ligand is chosen from the group consisting of peptides comprising the RGD motif or the NGR motif.

* * * * *